(12) United States Patent
Sgroi, Jr.

(10) Patent No.: US 11,457,921 B2
(45) Date of Patent: Oct. 4, 2022

(54) ANVIL ASSEMBLY FOR SURGICAL STAPLING INSTRUMENT

(71) Applicant: Covidien LP, Mansfield, MA (US)

(72) Inventor: Anthony Sgroi, Jr., Wallingford, CT (US)

(73) Assignee: Covidien LP, Mansfield, MA (US)

( * ) Notice: Subject to any disclaimer, the term of this patent is extended or adjusted under 35 U.S.C. 154(b) by 401 days.

(21) Appl. No.: 16/801,404

(22) Filed: Feb. 26, 2020

(65) Prior Publication Data

US 2020/0305880 A1  Oct. 1, 2020

Related U.S. Application Data

(60) Provisional application No. 62/823,924, filed on Mar. 26, 2019.

(51) Int. Cl.
| | |
|---|---|
| *A61B 17/068* | (2006.01) |
| *A61B 17/115* | (2006.01) |
| *A61B 17/00* | (2006.01) |
| *A61B 17/072* | (2006.01) |
| *A61B 17/29* | (2006.01) |

(52) U.S. Cl.
CPC . *A61B 17/1155* (2013.01); *A61B 2017/00477* (2013.01); *A61B 2017/07257* (2013.01); *A61B 2017/07271* (2013.01); *A61B 2017/07285* (2013.01); *A61B 2017/2927* (2013.01)

(58) Field of Classification Search
CPC .............. A61B 17/0293; A61B 17/115; A61B 17/1155; A61B 2017/07257

USPC ............................................. 227/176.1, 180.1
See application file for complete search history.

(56) References Cited

U.S. PATENT DOCUMENTS

| | | | |
|---|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

European Search Report dated Oct. 26, 2020, issued in EP Appln. No. 20165595, 15 pages.

(Continued)

*Primary Examiner* — Eyamindae C Jallow

(57) ABSTRACT

An anvil assembly for use with a circular stapling instrument includes an anvil center rod and an anvil head. The anvil head includes an anvil housing, a backup member and at least one retainer. The backup member is configured for longitudinal movement from an initial longitudinal position retaining the anvil head in a first operative condition to an advanced longitudinal position permitting pivotal movement of the anvil head to a second tilted condition.

26 Claims, 17 Drawing Sheets

(56) References Cited

U.S. PATENT DOCUMENTS

| | | |
|---|---|---|
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Billner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |

(56) References Cited

U.S. PATENT DOCUMENTS

| | | |
|---|---|---|
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |

(56) References Cited

U.S. PATENT DOCUMENTS

| | | |
|---|---|---|
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 9,554,802 B2 * | 1/2017 | Williams ........... A61B 17/1155 |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |

(56) References Cited

U.S. PATENT DOCUMENTS

| | | |
|---|---|---|
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0367444 A1* | 12/2014 | Williams ............ A61B 17/1155 227/175.1 |
| 2015/0305742 A1* | 10/2015 | Williams ............. A61B 17/072 227/177.1 |
| 2015/0366562 A1* | 12/2015 | Williams ............. A61B 17/064 227/175.1 |
| 2016/0143641 A1 | 5/2016 | Sapienza et al. |
| 2016/0157855 A1* | 6/2016 | Williams ............ A61B 17/1155 227/180.1 |
| 2016/0157856 A1 | 6/2016 | Williams et al. |
| 2016/0174988 A1 | 6/2016 | D'Agostino et al. |
| 2016/0302792 A1 | 10/2016 | Motai |
| 2017/0000475 A1* | 1/2017 | Sgroi, Jr ............ A61B 17/1155 |
| 2017/0020527 A1* | 1/2017 | Williams ............ A61B 17/1155 |
| 2017/0100124 A1* | 4/2017 | Williams ............ A61B 17/1155 |
| 2020/0337708 A1* | 10/2020 | Sgroi, Jr. ............ A61B 17/1155 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 2583631 A1 | 4/2013 |
| EP | 2959846 A1 | 12/2015 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

OTHER PUBLICATIONS

Partial European Search Report dated Jul. 24, 2020, issued in EP Appln. No. 20165595, 18 pages.

* cited by examiner

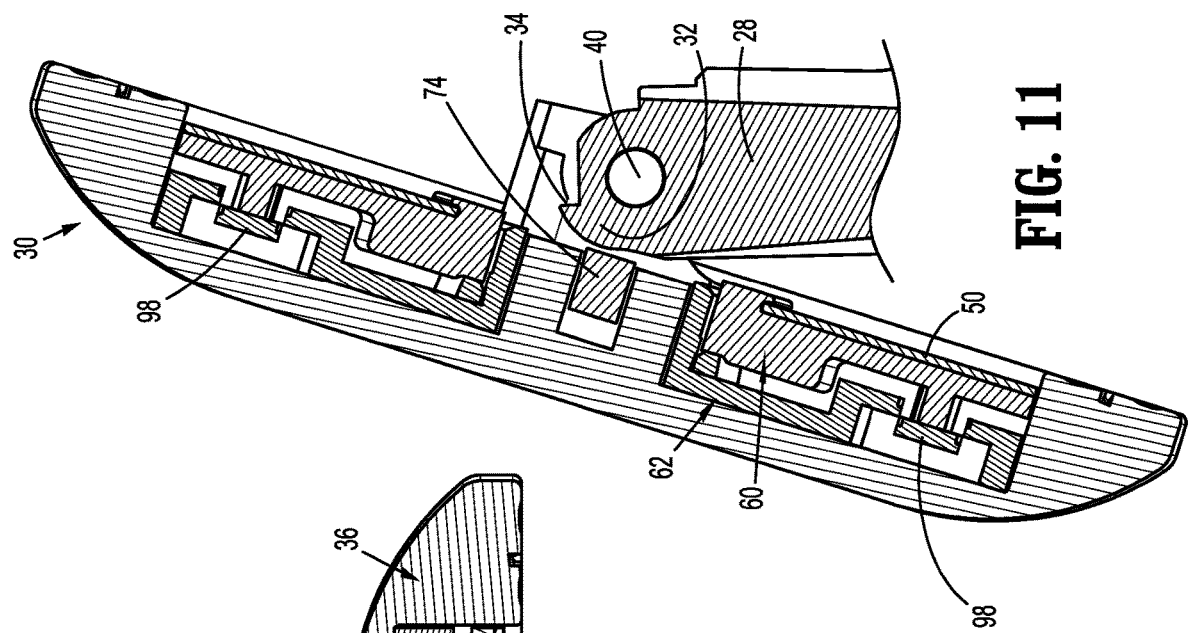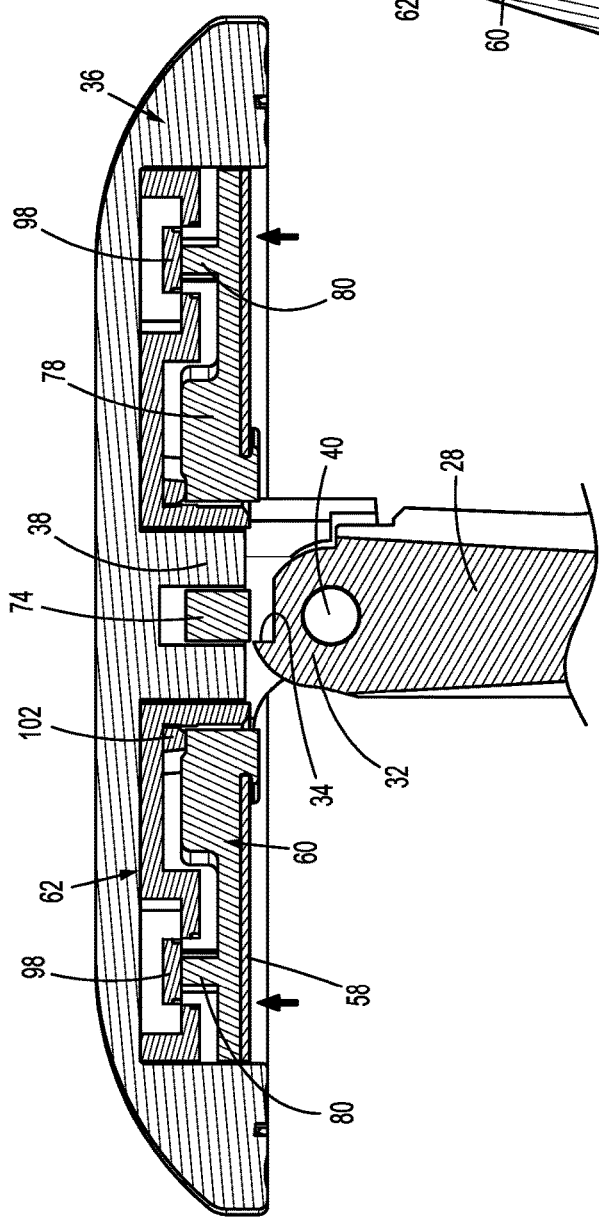

ANVIL ASSEMBLY FOR SURGICAL STAPLING INSTRUMENT

CROSS-REFERENCE TO RELATED APPLICATIONS

This application claims the benefit of and priority to U.S. Provisional Patent Application Ser. No. 62/823,924 filed Mar. 26, 2019, the entire disclosure of which is incorporated by reference herein

BACKGROUND

1. Technical Description

The disclosure generally relates to a surgical stapling instrument and, more particularly, relates to an anvil assembly for use with a circular stapling instrument having an anvil head capable of pivoting or tilting upon actuation of the stapling instrument to facilitate insertion and/or withdrawal of the anvil assembly relative to the operative site.

2. Background of Related Art

Surgical stapling instruments for performing surgical procedures such as anastomoses, hemorrhoidectomies, and mucosectomies are well known. In a circular anastomosis procedure, two ends of organ sections are joined with a circular stapling instrument. Typically, these circular stapling instruments include a handle, an elongated shaft with a staple holding component, and an anvil assembly mountable to the staple holding component. The anvil assembly includes an anvil center rod and an attached anvil head which may be pivotal relative to the anvil center rod to facilitate insertion and removal of the anvil assembly relative to the organ sections. In use, opposed tissue end margins of the organ sections are clamped between the anvil head and the staple holding component. The instrument is fired which drives an annular array of staples from the staple holding component through the tissue end margins of the organ sections for deformation against the anvil head. An annular knife within the staple holding component is advanced to core or remove organ tissue interior of the staples to clear the internal tubular passage of the organ sections. Thereafter, the anvil head may be tilted relative to the anvil center rod to facilitate withdrawal of the anvil assembly from within the attached organ sections. An example of an instrument for performing circular anastomosis of tissue is disclosed in commonly assigned U.S. Pat. No. 9,750,503, the entire contents of which is incorporated by reference herein.

SUMMARY

One aspect of the disclosure is directed to a surgical anvil assembly for use with a circular stapling instrument including an anvil center rod and an anvil head pivotally coupled to the anvil center rod and movable between a first operative condition and a second tilted condition. The anvil head includes an anvil housing defining a central longitudinal axis, a backup member disposed within the anvil housing, and a retainer positioned in the anvil housing adjacent the backup member. The backup member is configured for longitudinal movement relative to the anvil housing from an initial longitudinal position retaining the anvil head in the first operative condition to an advanced longitudinal position permitting pivotal movement of the anvil head to the second tilted condition. The backup member includes an outer plate segment having a plurality of force transfer projections. The retainer is configured to retain the backup member in the initial longitudinal position. The retainer includes an outer retainer segment defining an outer deformable region in general longitudinal alignment with the force transfer projections of the backup member. The outer deformable region is configured to be engaged by the force transfer projections of the backup member and at least partially deform upon application of a predetermined longitudinal force to the backup member to permit the backup member to move to the advanced longitudinal position.

In embodiments, the anvil housing includes a housing wall with the retainer being at least partially positioned between the housing wall and the backup member. In some embodiments, the force transfer projections of the backup member are coaxially arranged with respect to the central longitudinal axis. In certain embodiments, the outer deformable region of the retainer is coaxially arranged about the central longitudinal axis. In embodiments, the outer retainer segment includes at least two grooves defined therein whereby the outer deformable region is defined at least in part between the two grooves. In some embodiments, the at least two grooves are annular and coaxially arranged about the central longitudinal axis.

In certain embodiments, the outer deformable region of the retainer is configured to fracture relative to the outer retainer segment upon engagement with the force transfer projections of the backup member upon application of the predetermined longitudinal force to the backup member.

In embodiments, the retainer includes an inner deformable ring radial inward of the outer deformable region. The inner deformable ring is configured to be engaged by the backup member and at least partially deform upon application of the predetermined longitudinal force to the backup member. In some embodiments, the inner deformable ring is configured to fracture upon application of the predetermined longitudinal force to the backup member.

In certain embodiments, a cut ring is positioned adjacent the backup member. In embodiments, the anvil head includes an anvil post depending from the housing wall, wherein the retainer, the backup member and the cut ring are coaxially mounted about the anvil post.

Another aspect of the disclosure is directed to an end effector for use with a circular stapling instrument is disclosed. The end effector includes a cartridge assembly and an anvil assembly mountable relative to the cartridge assembly. The cartridge assembly includes a cartridge housing and an annular knife configured for advancing movement relative to the cartridge housing from an unactuated position to an actuated position. The anvil assembly includes an anvil center rod and an anvil head pivotally coupled to the anvil center rod and movable between a first operative condition and a second tilted condition. The anvil head includes an anvil housing defining a central longitudinal axis, a backup member disposed within the anvil housing, and a retainer positioned in the anvil housing adjacent the backup member. The backup member is configured for longitudinal movement relative to the anvil housing from an initial longitudinal position retaining the anvil head in the first operative condition to an advanced longitudinal position permitting pivotal movement of the anvil head to the second tilted condition upon advancing movement of the annular knife toward the actuated position. The backup member includes an outer plate segment having a plurality of force transfer projections coaxially arranged with respect to the central longitudinal axis. The retainer is configured to retain the backup member in the initial longitudinal position. The retainer includes an outer retainer segment defining an annular deformable region coaxially arranged with respect to the central longitudinal axis and in general longitudinal alignment with the force transfer projections of the backup member. The annular deformable region is configured to be engaged by the force transfer projections of the backup member and at least partially deform upon advancing movement of the annular knife toward the actuated position to permit the backup member to move to the advanced longitudinal position.

In embodiments, the retainer includes an inner deformable ring radial inward of the annular deformable region, and configured to be engaged by the backup member and at least partially deform upon advancing movement of the annular knife toward the actuated position. In some embodiments, the annular deformable region and the inner deformable ring are each configured to fracture upon advancing movement of the annular knife toward the actuated position. In certain embodiments, the backup member includes a pair of diametrically opposed fingers configured for engagement with the anvil center rod in the initial longitudinal position of the backup member to maintain the anvil head in the first operative condition, and configured to release the anvil center rod upon movement to the advanced longitudinal position to permit pivoting movement of the anvil head to the second tilted condition.

The components of the backup member and the retainer of the disclosed anvil assembly cooperate to ensure that deformation and/or fragmentation of the retainer is achieved when the backup member is subjected to a predetermined force, e.g., an advancing annular knife, to permit complete release of the anvil rod and subsequent pivotal movement of the anvil head to the tilted condition.

Another aspect of the present disclosure is directed to a surgical anvil assembly for use with a circular stapling instrument including an anvil center rod and an anvil head. The anvil head is pivotally coupled to the anvil center rod and is movable between a first operative condition and a second tilted condition. The anvil head includes an anvil housing, a backup member, an inner retainer, and an outer retainer. The anvil housing defines a central longitudinal axis and a cavity defined by a distal wall surface. The backup member is disposed within the anvil housing and has an inner circumferential surface and an outer circumferential surface. The backup member is movable from an initial longitudinal position in which the backup member retains the anvil head in the first operative condition to an advanced longitudinal position in which the backup member permits pivotal movement of the anvil head to the second tilted condition. The inner retainer is positioned in the anvil housing adjacent the backup member to engage the inner circumferential surface of the backup member to retain the backup member in the initial longitudinal position. The inner retainer includes a breakaway zone that is frangible upon application of a predetermined distal force on the backup member to permit movement of the backup member to the advanced longitudinal position. The outer retainer is positioned in the anvil housing adjacent the backup member to engage the outer circumferential surface of the backup member to retain the backup member in the initial longitudinal position. The outer retainer includes a frangible portion that is frangible upon application of a predetermined distal force on the backup member to permit movement of the backup member to the advanced longitudinal position.

In embodiments, the inner retainer includes an annular body having a distal portion that is positioned in abutting relation to the distal wall surface of the housing.

In some embodiments, the inner retainer includes a support member that supports the inner circumferential surface of the backup member, wherein the support member is coupled to the annular body by a connecting segment that includes the breakaway zone.

In certain embodiments, the support member includes a plurality of support members spaced about the annular body.

In embodiments, the outer retainer includes a body having a proximal step and a distal step, wherein the distal step includes an abutment surface that is positioned to abut the distal wall surface defining the cavity and the proximal step includes a support surface positioned to support the outer circumferential surface of the backup member.

In some embodiments, the outer step includes the frangible portion.

In certain embodiments, a cut ring is supported on a distal face of the backup member.

Another aspect of the disclosure is directed to a surgical anvil assembly for use with a circular stapling instrument including an anvil center rod and an anvil head. The anvil head is pivotally coupled to the anvil center rod and is movable between a first operative condition and a second tilted condition. The anvil head includes an anvil housing, a backup member, a cut ring, a backup washer, a compliant washer, and a retainer. The anvil housing defines a central longitudinal axis and a cavity defined by a distal wall surface. The backup member is disposed within the anvil housing and includes an inner circumferential surface and an outer circumferential surface. The backup member is movable from an initial longitudinal position in which the backup member retains the anvil head in the first operative condition to an advanced longitudinal position in which the backup member permits pivotal movement of the anvil head to the second tilted condition. The compliant washer is supported on a distal face of the backup member. The backup washer is supported on a distal face of the compliant washer and is formed of a metal. The cut ring is supported on a distal face of the backup washer. The retainer is positioned in the anvil housing adjacent the backup member and is positioned to engage the backup member to retain the backup member in the initial longitudinal position. The retainer is deformable or frangible upon application of a predetermined distal force on the backup member to permit movement of the backup member to the advanced longitudinal position, wherein the backup washer is configured to deform into the compliant washer upon application of a predetermined force on the backup washer.

In some embodiments, the backup washer has a thickness of about 0.0254 mm to about 0.762 mm with about 0.254 mm being most preferred and includes any sub-ranges therebetween.

In some embodiments, the compliant washer is formed from rubber.

In certain embodiments, the backup washer is formed from stainless steel.

In embodiments, the retainer is positioned to engage the inner circumferential surface of the retainer.

Other features of the disclosure will be appreciated from the following description.

BRIEF DESCRIPTION OF THE DRAWINGS

Various embodiments of the disclosed anvil assembly for use with a surgical circular stapling instrument are described herein below with reference to the drawings, wherein:

FIG. 10 is a cross-sectional view similar to the view of FIG. 6 illustrating the backup member in the advanced longitudinal position with the anvil rod released from the fingers of the backup member to permit pivotal movement of the anvil head;

FIG. 11 is a side cross-sectional view of the anvil assembly shown in FIG. 10 illustrating the anvil head in a second tilted condition;

DETAILED DESCRIPTION OF EMBODIMENTS

Figure 1:
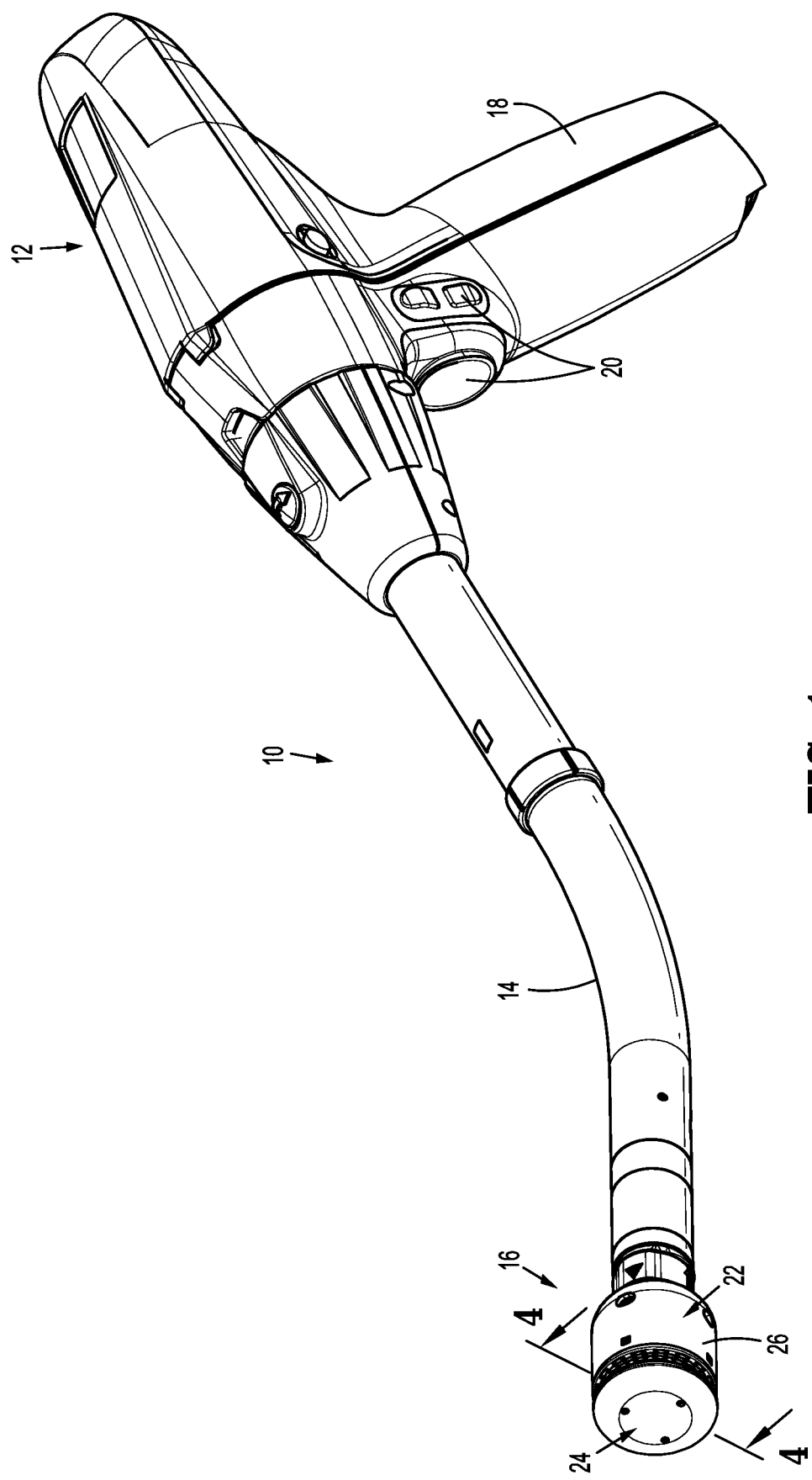
FIG. 1 is a perspective view of a surgical circular stapling instrument incorporating an end effector having an exemplary embodiment of an anvil assembly according to the disclosure.

Embodiments of the disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to that portion of the instrument or component thereof that is closest to the clinician and the term "distal" refers to that portion of the instrument or component thereof that is farthest from the clinician. In addition, the term "about" means between 90 and 110 percent of the identified parameter.

The exemplary surgical stapling instrument includes a handle assembly, an elongate body or adapter extending from the handle assembly and an end effector couplable to the adapter. The end effector includes a cartridge assembly having an annular array of staples and an annular knife, and an anvil assembly. The anvil assembly includes an anvil center rod releasably couplable to the cartridge assembly and an anvil head which is pivotally coupled to the anvil center rod. The anvil head includes an anvil housing which accommodates a backup member and a deformable or frangible retainer disposed distal of the backup member. A cut ring may be disposed proximal of the backup member. The retainer maintains the backup member in operative engagement with the anvil center rod thereby securing the anvil head in an operative condition in opposition to the cartridge assembly prior to firing of the instrument. In use, the tissue end margins of the tubular organ sections to be joined are positioned about the anvil head and the cartridge assembly, respectively. The anvil head and the cartridge assembly are approximated, and the instrument is actuated causing ejection of the staples and advancing movement of the annular knife through the tissue end margins supported by the cut ring and the backup member of the anvil head. Advancement of the annular knife causes the backup member to also advance relative to the anvil housing and engage the retainer to deform and/or fracture the retainer. This deformation of the retainer releases the backup member from its operative engagement with the anvil center rod thereby permitting the anvil head to move to a tilted or pivoted condition. The retainer and the backup member include multiple cooperating structures which captures and directly transfers the forces exerted by the annular knife to provide precise deformation and/or fracturing of the retainer to ensure the backup member completely releases the anvil rod to permit unencumbered pivotal movement of the anvil head.

Figure 2:
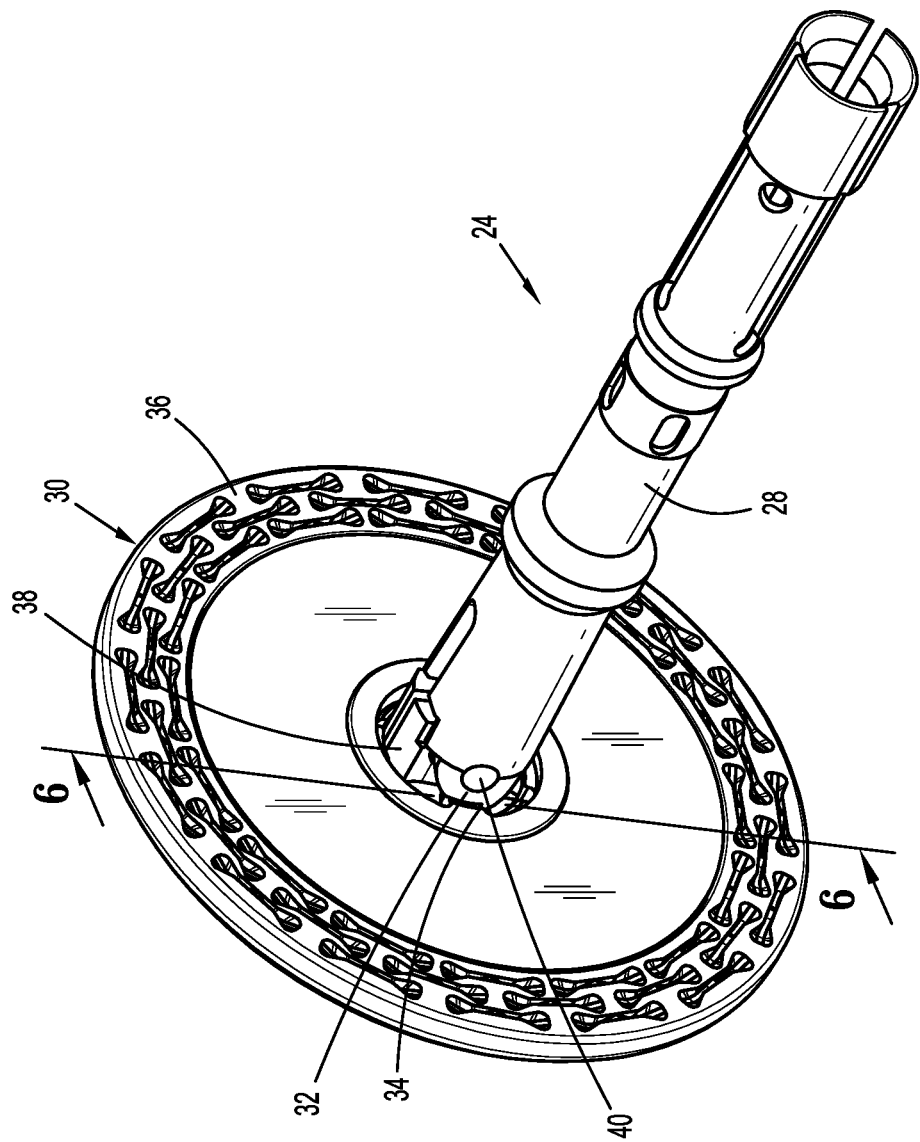
FIG. 2 is a perspective view of the anvil assembly of the stapling instrument shown in FIG. 1.

Referring to FIGS. 1-2, the circular stapling instrument incorporating the end effector and the anvil assembly of the disclosure is illustrated and shown generally as circular stapling instrument 10. The circular stapling instrument 10 includes a handle 12, an elongate body or adapter 14 extending from the handle 12, and an end effector 16 coupled to the adapter 14. The handle 12 may be electrically powered and include a motor and associated gears and linkages to control operation of the stapling instrument 10. The handle 12 incorporates a grip 18 and a plurality of actuation buttons 20 which may be activated to control various functions of the stapling instrument 10 including, e.g., approximation of the end effector 16 and firing of staples. The grip 18 may support a battery pack (not shown) which powers the handle 12. It is also envisioned that the handle 12 could be manually powered. Examples of manually powered handle assemblies are described in commonly assigned U.S. Pat. Nos.: 8,360,295; 8,424,535; and 8,789,737, which are incorporated in their respective entireties by reference herein.

In embodiments, the adapter 14 is releasably coupled to the handle 12 and includes a plurality of drive mechanisms (not shown) that translate power from the handle 12 to the end effector 16 in response to actuation of the actuation buttons 20 to effect operation, i.e., approximation and firing, of the end effector 16. Commonly assigned U.S. Pat. Nos.: 8,806,973; 9,055,943; 9,247,940; and 9,629,633 disclose exemplary embodiments of powered handles and adapters suitable for use with the stapling instrument 10, and which are incorporated in their respective entireties by reference herein. Alternately, the elongate body or adapter 14 can be non-removably secured to the handle 12.

The end effector 16 includes a cartridge assembly 22 and an anvil assembly 24 couplable relative to the cartridge assembly 22. In general, the cartridge assembly 22 incorporates a cartridge housing 26, one or more annular rows of staples (not shown) within the cartridge housing 26, staple pushers (not shown) for advancing the staples through the tissue end margins of the tubular organ sections and an annular knife (not shown in FIG. 1) internal of the staples to sever and remove excess organ tissue within the tubular organ sections upon advancement of the annular knife during, or subsequent to, deployment of the staples.

Figure 3:
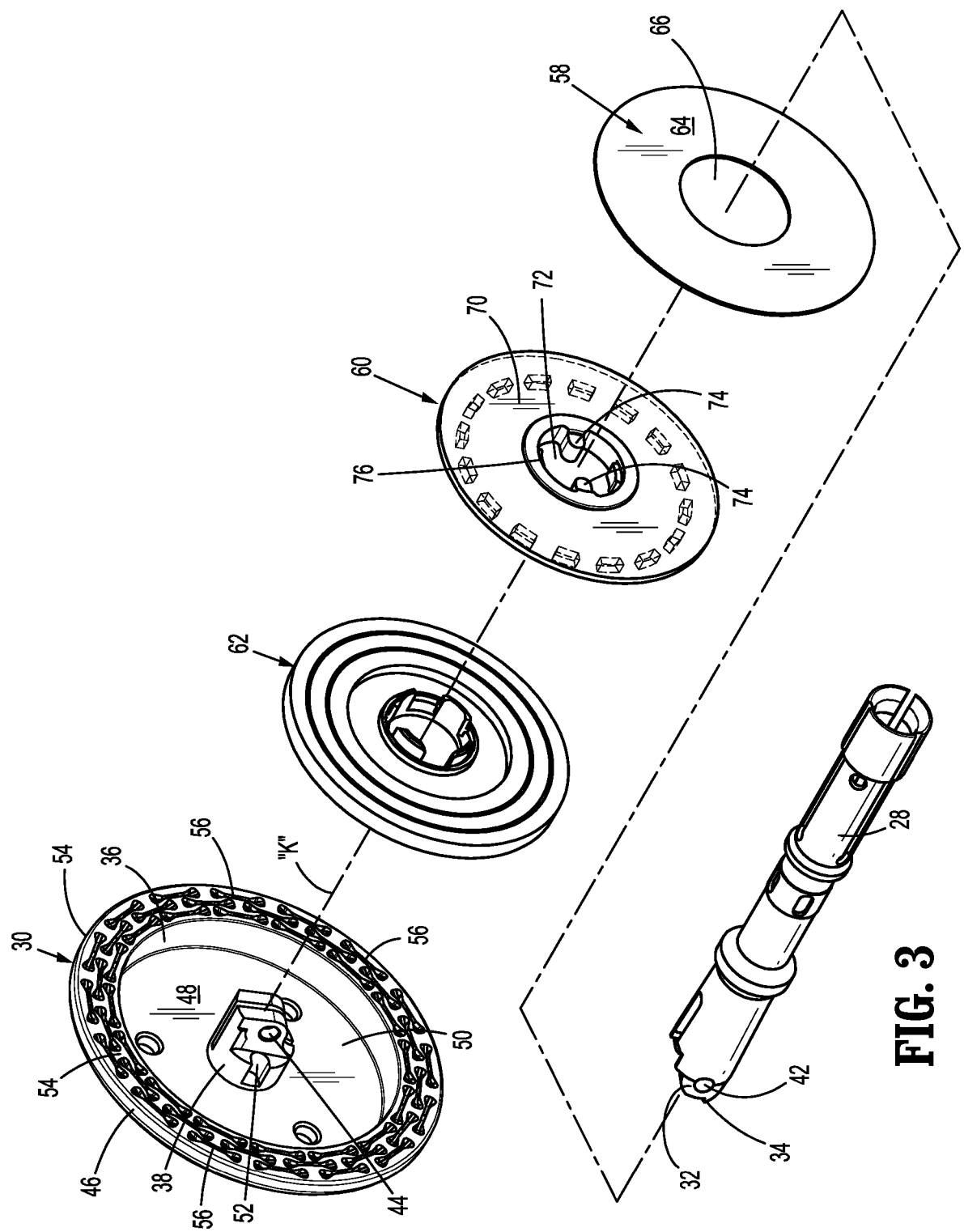
FIG. 3 is an exploded, perspective view of the anvil assembly shown in FIG. 2.
Figure 4:
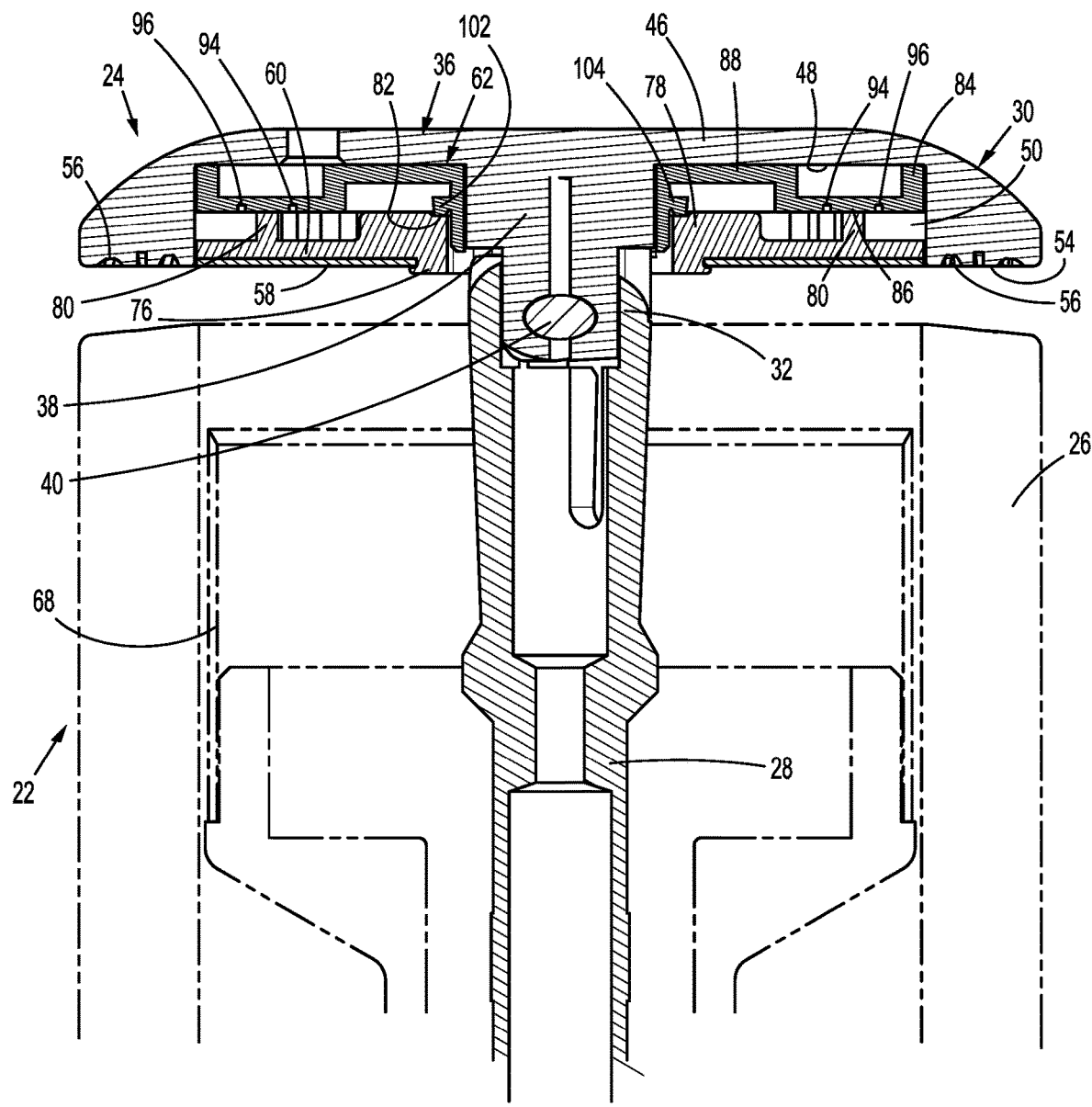
FIG. 4 is a cross-sectional view of the end effector taken along section line 4-4 of FIG. 1.

Referring now to FIGS. 2-4, the anvil assembly 24 of the end effector 16 will be described. The anvil assembly 24 shares some common features with the anvil assembly disclosed in commonly assigned U.S. Pat. No. 8,540,132 ("132 Patent"), the entire contents of which are incorporated by reference herein. The anvil assembly 24 includes an anvil center rod 28 and an anvil head 30 pivotally mounted to the anvil center rod 28. The anvil center rod 28 includes a pair of spaced arms 32 with distal shelves 34. The anvil head 30 is adapted to pivot relative to the anvil center rod 28 between a first operative condition in opposition to the cartridge assembly 22 (as depicted in FIG. 1) and a second pivoted or tilted condition, and may be normally biased to the second titled condition via a spring-biased plunger mechanism (not shown). The anvil head 30 includes an anvil housing 36 with an internal anvil post 38 which is at least partially received within the spaced arms 32 of the anvil center rod 28. A pivot pin 40 extends through respective transverse bores 42, 44 of the spaced arms 32 and the anvil post 38 to pivotally couple the anvil head 30 to the anvil center rod 28.

With reference to FIGS. 3-4, the anvil housing 36 of the anvil assembly 24 defines a central longitudinal axis "k" along which the anvil post 38 extends. The anvil housing 36 includes a distal housing wall 46 defining an internal wall surface 48 which supports the anvil post 38, and an internal housing recess 50. The anvil post 38 includes at least one keyed slot 52 and, in embodiments, includes a pair of diametrically opposed keyed slots 52. The anvil housing 36 includes an outer tissue contact surface 54 circumscribing the internal housing recess 50. The outer tissue contact surface 54 supports tissue end margins of a tubular organ section, and incorporates a plurality of staple deforming pockets 56 to receive and deform staples ejected from the cartridge housing 26 of the cartridge assembly 22.

The anvil head 30 includes, from proximal to distal, a cut ring 58, a backup member 60 and a frangible or deformable retainer 62, each being disposed within the internal housing recess 50 of the anvil housing 36 and coaxially arranged about the anvil post 38 (FIG. 3). The cut ring 58 includes a disc-shaped annular body 64 defining a central aperture 66 for reception of the anvil post 38. The cut ring 58 is at least partially penetrated by the annular knife during firing of the stapling instrument 10 such that the tissue end margins overlying the cut ring 58 are severed by the annular knife to create a passage through the anastomosed tubular organ sections. In embodiments, the cut ring 58 is formed through a molding process, e.g., an injection molding process, and may be fabricated from a material having a durometer which permits the annular knife to pierce completely through the annular body 64 and bottom out against the backup member 60. Suitable materials include polypropylene or polyester. Other materials are also contemplated.

The backup member 60 will be discussed with reference to FIGS. 3-6. The backup member 60 is configured for longitudinal movement relative to the anvil housing 36 from an initial longitudinal position to an advanced longitudinal position upon movement of the annular knife 68 (FIG. 4) within the cartridge housing 26 toward its actuated position. The backup member 60 includes an outer plate segment 70 defining a central aperture 72 dimensioned for positioning about the anvil post 38 of the anvil housing 36. The backup member 60 includes a pair of diametrically opposed fingers 74 extending radially inwardly from the outer plate segment 70 and within the central aperture 72. As best depicted in FIG. 6, the fingers 74 are at least partially received within the diametrically opposed keyed slots 52 of the anvil post 38 to align and/or support the backup member 60 relative to the anvil housing 36. The fingers 74 also engage the distal shelves 34 of the spaced arms 32 of the anvil center rod 28 to prevent pivotal movement of the anvil head 30 about the pivot pin 40 and maintain the anvil head 30 in a first operative condition in opposition to the cartridge assembly 22.

As best depicted in FIG. 3, the proximal side of the outer plate segment 70 of the backup member 60 includes a proximal raised flange 76 circumscribing the central aperture 72 which is received within the central aperture 66 of the cut ring 58. The proximal raised flange 76 of the backup member 60 may be press fit within the central aperture 66 of the cut ring 58 to secure these components to each other. Alternatively, the backup member 60 and the cut ring 58 may be coupled with cements, adhesives, spot welding or the like. In embodiments, the backup member 60 and the cut ring 58 are not secured to each other.

Figure 5:
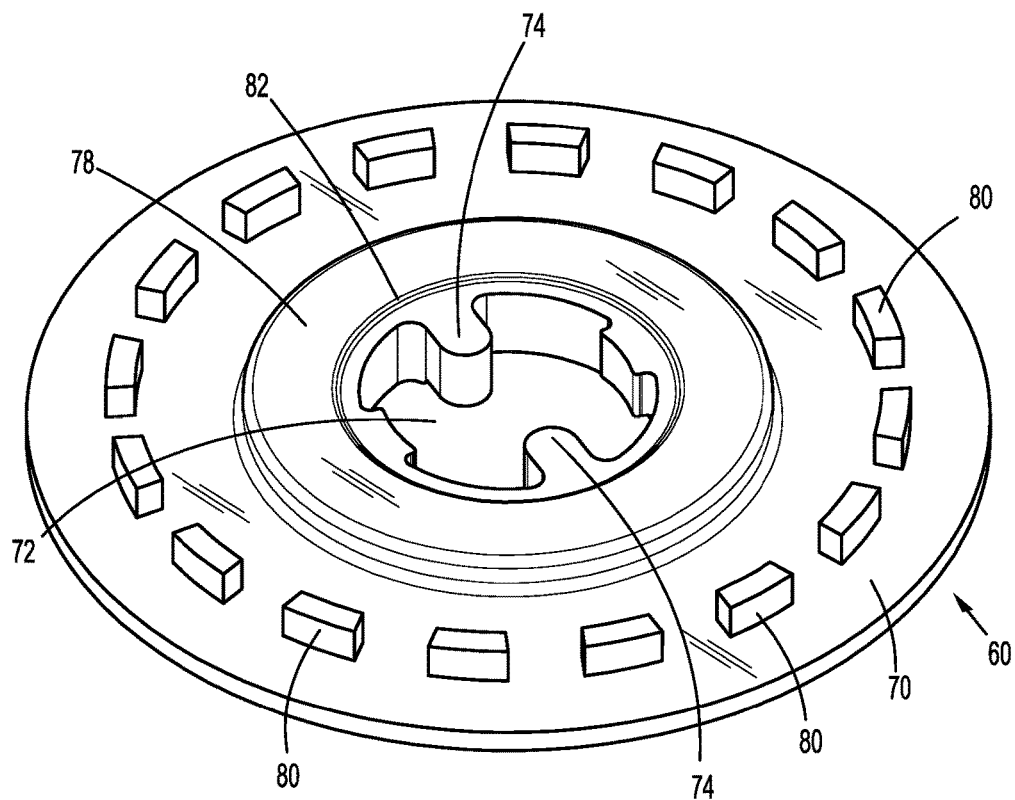
FIG. 5 is a perspective view of the backup member of the anvil assembly shown in FIG. 3.
Figure 6:
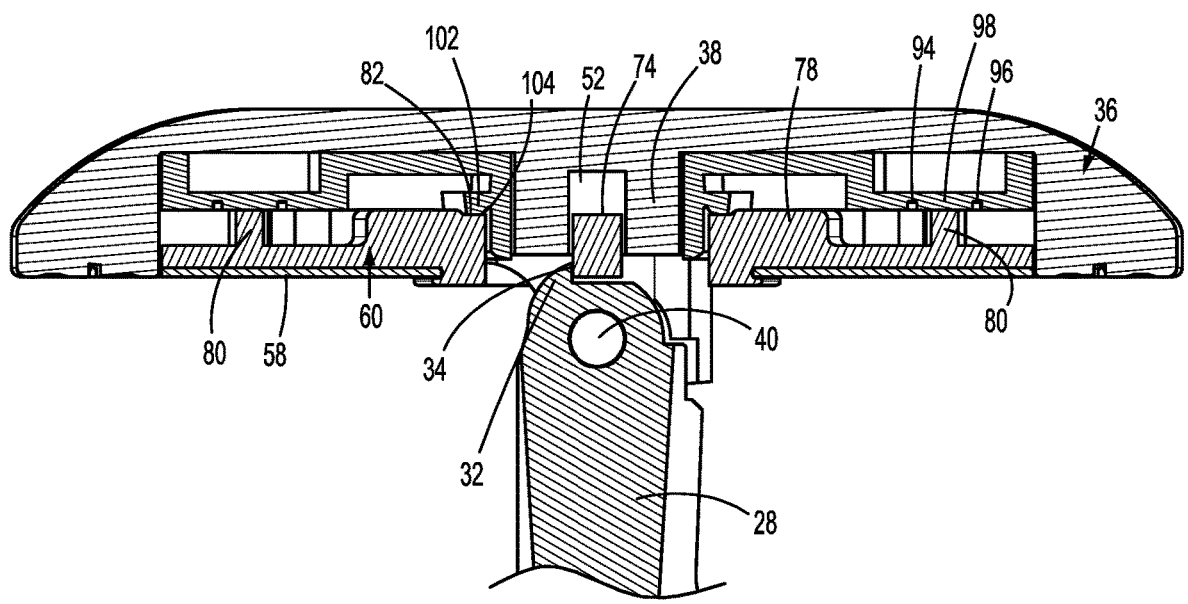
FIG. 6 is a cross-sectional view of an anvil head of the anvil assembly shown in FIG. 3 taken along section line 6-6 of FIG. 2.

With reference to FIGS. 4-6, the distal side of the backup member 60 includes a distal raised flange 78 circumscribing the central aperture 72 and a plurality of force transfer projections 80 that are positioned radially outward of the distal raised flange 78 and extend in a longitudinal direction from the outer plate segment 70. The distal raised flange 78 may define an annular recessed surface 82 adjacent the central aperture 72. The force transfer projections 80 may be coaxially oriented about the central longitudinal axis "k" of the anvil housing 36 to define an annular or ring-like configuration as shown, and may be equal distantly spaced relative to each other. The force transfer projections 80 may be generally box-like (e.g., rectangular box) in shape although other shapes and sizes are also contemplated. The backup member 60 may be formed from a hard material such as metal although other materials of construction are envisioned.

Figure 7:
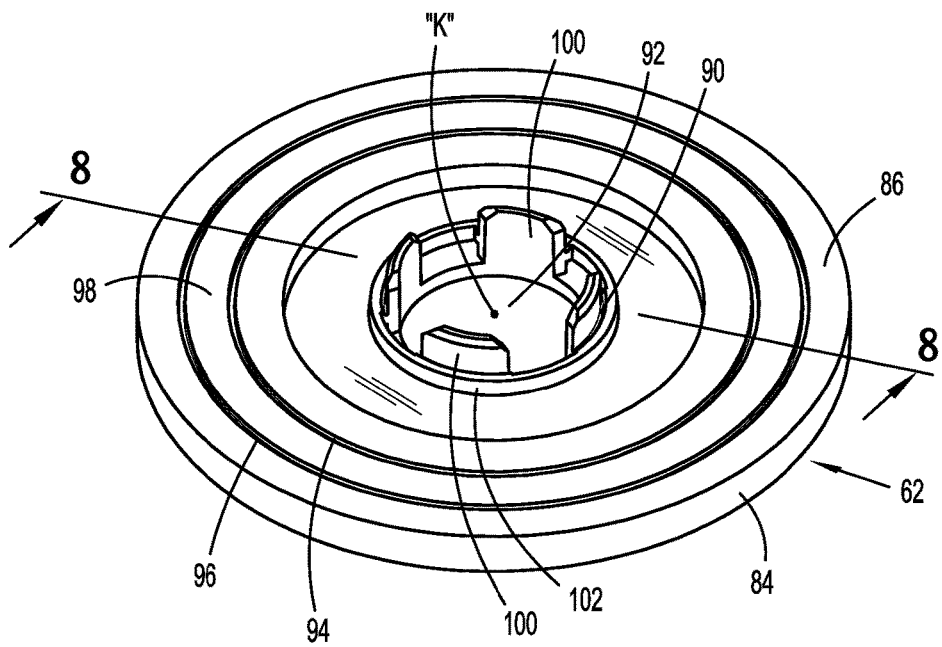
FIG. 7 is a perspective view of a retainer of the anvil assembly shown in FIG. 3.
Figure 8:
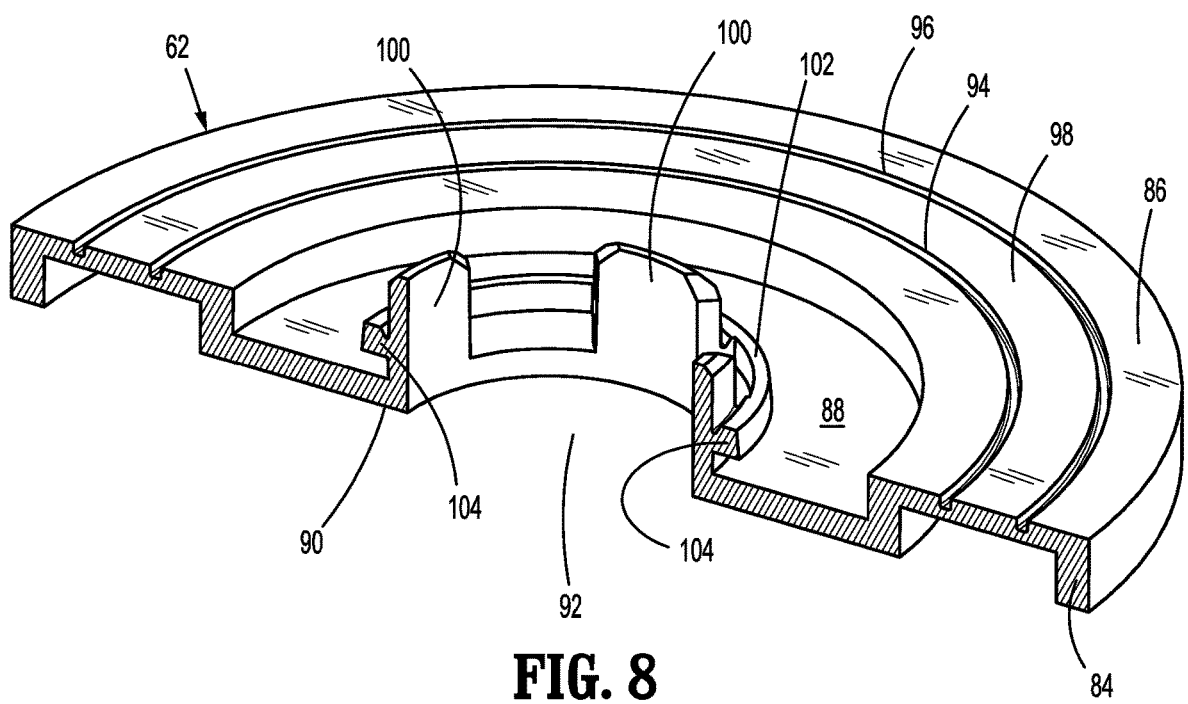
FIG. 8 is a perspective view in partial cross-section taken along section line 8-8 of FIG. 7.

With reference to FIGS. 7-8, in conjunction with FIG. 4, the retainer 62 will be discussed. The retainer 62 is coaxially disposed about the anvil post 38 between the backup member 60 and the internal wall surface 48 of the anvil housing 36. The retainer 62 defines an outer peripheral wall 84, an outer retainer segment 86 positioned radially inward of the peripheral wall 84, an intermediate retainer segment 88 recessed relative to the outer retainer segment 86 and an inner retainer segment 90 inward of the intermediate retainer segment 88. The inner retainer segment 90 defines a central aperture 92 for receiving the anvil post 38. The outer retainer segment 86 has first and second grooves 94, 96 defined therein that are coaxially arranged relative to the central longitudinal axis "k". The first and second grooves 94, 96 are radially spaced to define a deformable region 98 there between. The deformable region 98 is in general longitudinal alignment with the force transfer projections 80 of the backup member 60, and at least partially deforms or fragments along the first and second grooves 94, 96 upon actuation of the annular knife 68 through engagement with the force transfer projections 80.

The inner retainer segment 90 includes a plurality (e.g., four) of tabs 100 depending in a proximal direction for reception within the central aperture 72 of the backup member 60. The tabs 100 stabilize the retainer 62 relative to the backup member 60. An inner deformable ring 102 is coupled to the tabs 100 and arranged in coaxial relationship with respect to the central longitudinal axis "k". In embodiments, the inner deformable ring 102 is coupled to each tab 100 via a connecting segment 104 extending between respective tabs 100 and the inner deformable ring 102. The connecting segments 104 define breakaway zones along which the inner deformable ring 102 deforms or fragments relative to the tabs 100 upon actuation of the annular knife 68. The inner deformable ring 102 is spaced relative to the surface of the intermediate retainer segment 88 and may reside against the recessed surface 82 of the backup member 60. The retainer 62 may be monolithically formed of a suitable elastomeric or metallic material.

FIG. 4 illustrates the relationships of the components of the anvil assembly 24 prior to actuation of the annular knife 68 of the cartridge assembly 22 and with the backup member 60 in the initial longitudinal position. In the initial longitudinal position, the outer peripheral wall 84 and the intermediate retainer segment 88 of the retainer 62 are in engagement with the internal wall surface 48 of the anvil housing 36 and the outer retainer segment 86 and the inner deformable ring 102 of the retainer 62 are engaged with the backup member 60. This arrangement maintains the backup member 60 in a retracted position within the anvil housing 36 which corresponds to the initial longitudinal position of the backup member 60 and the first operative condition of the anvil head 30.

Figure 9:
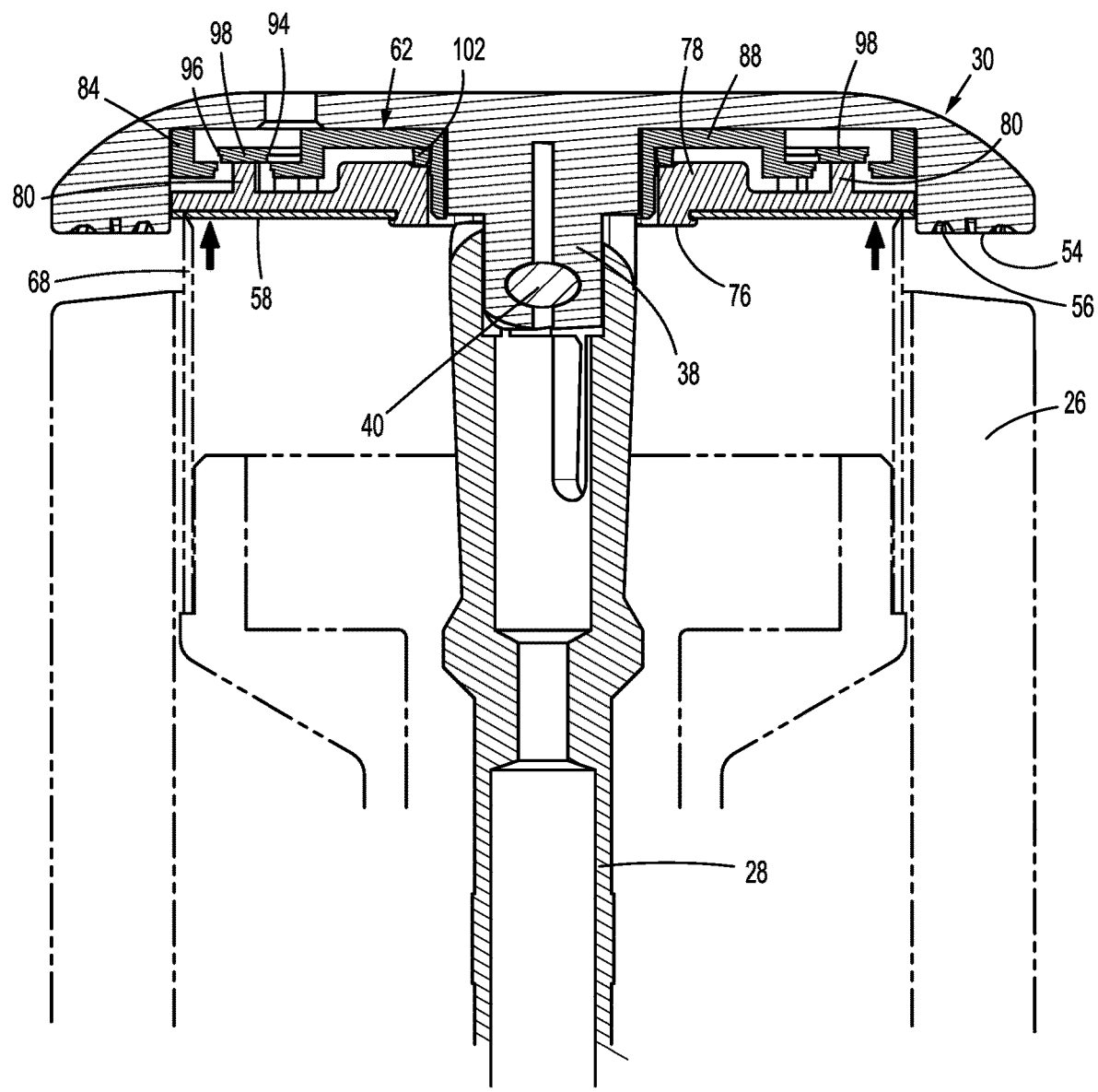
FIG. 9 is a cross-sectional view of the end effector similar to the view of FIG. 4 illustrating the backup member in an advanced longitudinal position upon actuation of the annular knife of the end effector to at least partially deform the retainer of the anvil assembly.

The use of the end effector 16 will now be discussed. The tissue end margins of the tubular organ sections to be joined are placed about the anvil head 30 and the cartridge housing 26 of the cartridge assembly 22, respectively and secured via a purse string stitch or any other conventional methodology. The anvil head 30 and the cartridge assembly 22 are approximated. The stapling instrument 10 is then fired to eject the staples from the cartridge assembly 22 for passage through the tissue end margins of the tubular organ sections and deformation against the staple deforming pockets 56 of the anvil housing 3. The annular knife 68 is actuated to advance the annular knife 68 from the unactuated position of FIG. 4 within the cartridge assembly 22 to the actuated position of FIG. 9 extending through the tissue end margins and at least partially or completely through the cut ring 58. As the annular knife 68 advances, the backup member 60 is advanced toward the advanced longitudinal position. This motion causes: 1) the force transfer projections 80 of the backup member 60 to exert a force on the deformable region 98 defined between the coaxial first and second grooves 94, 96 of the retainer 62 sufficient to cause deformation and/or fragmentation of the outer deformable region 98 of the retainer 62 along the grooves 94, 96; and 2) the distal raised flange 78 of the backup member 60 to deform and/or fragment the inner deformable ring 102 along the connecting segments 104. As best depicted in FIG. 10, the deformation of the retainer 62 also permits the backup member 60 and, possibly, the cut ring 58 to advance along the anvil post 38 with the fingers 74 of the backup member 60 traversing the keyed slots 52 of the anvil post 38. This movement releases the fingers 74 from their engagement with the distal shelves 34 of the spaced arms 32 of the anvil center rod 28. Thus, the anvil head 30 may pivot from the first operative condition in which the anvil head 30 is in opposition to the cartridge assembly 22 (FIG. 1) to a second tilted condition depicted in FIG. 10. A spring biased plunger mechanism may be associated with the anvil center rod 28 to bias the anvil head 30 and cause pivoting movement about the pivot pin 40 to assume the second tilted condition depicted in FIG. 10. Details of the plunger mechanism may be ascertained by reference to U.S. Pat. No. 8,540,132.

The backup member 60 transmits the forces exerted by the advancing annular knife 68 uniformly across the retainer 62 to deform or fragment the retainer 62 sufficiently to effect advancing movement of the backup member 60 within the anvil housing 36 and release of the anvil center rod 28. Specifically, the annular and aligned arrangements of the force transfer projections 80 and the distal raised flange 78 of the backup member 60 and the respective deformable region 98 and the inner deformable ring 102 of the retainer 62, ensures the forces generated by the advancing annular knife 68 are captured and directly conveyed to cause complete deformation and/or fragmentation of the retainer 62 to permit desired pivotal movement of the anvil head 30 to the second tilted condition.

Figure 12:
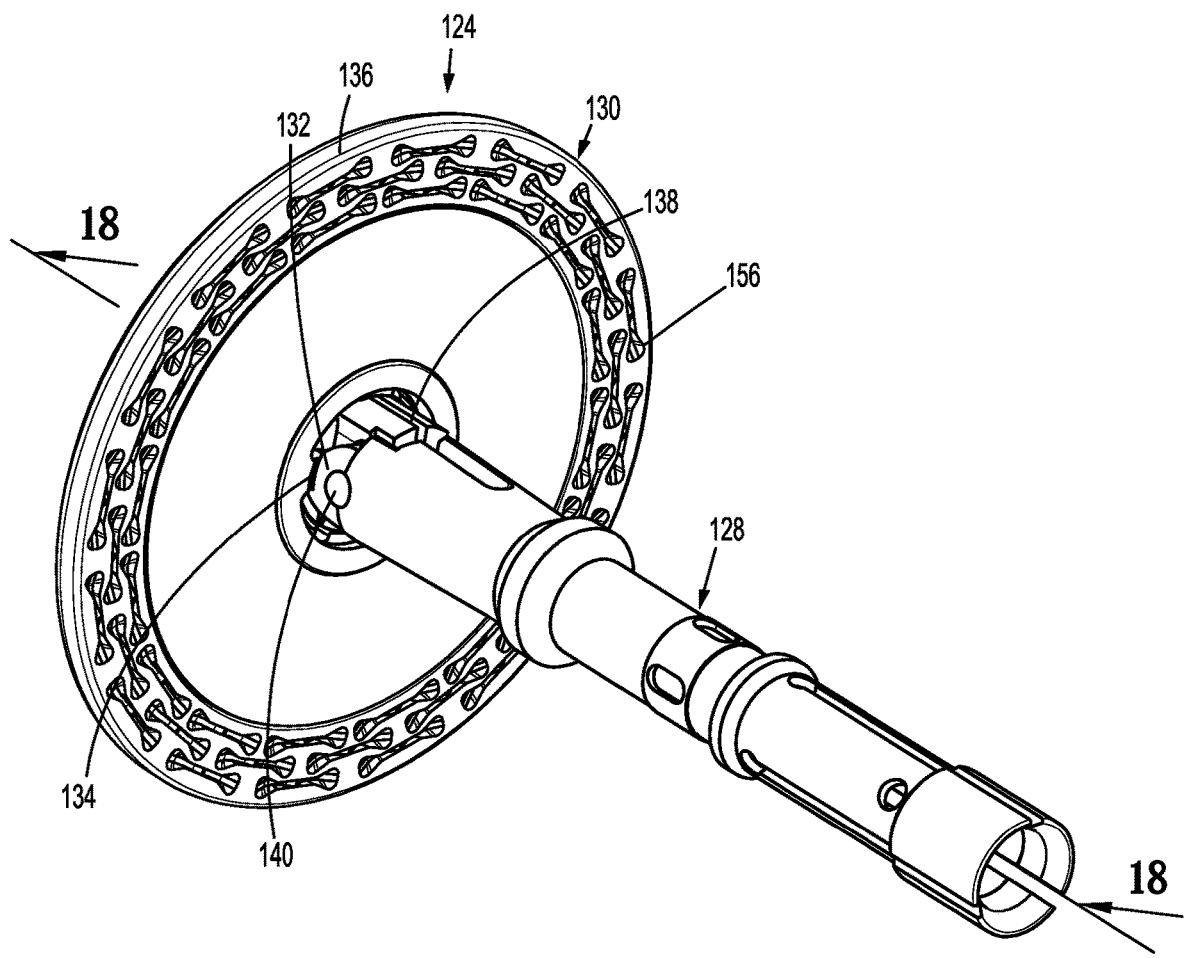
FIG. 12 is a perspective view of another exemplary embodiment of the anvil assembly of the stapling instrument shown in FIG. 1.
Figure 13:
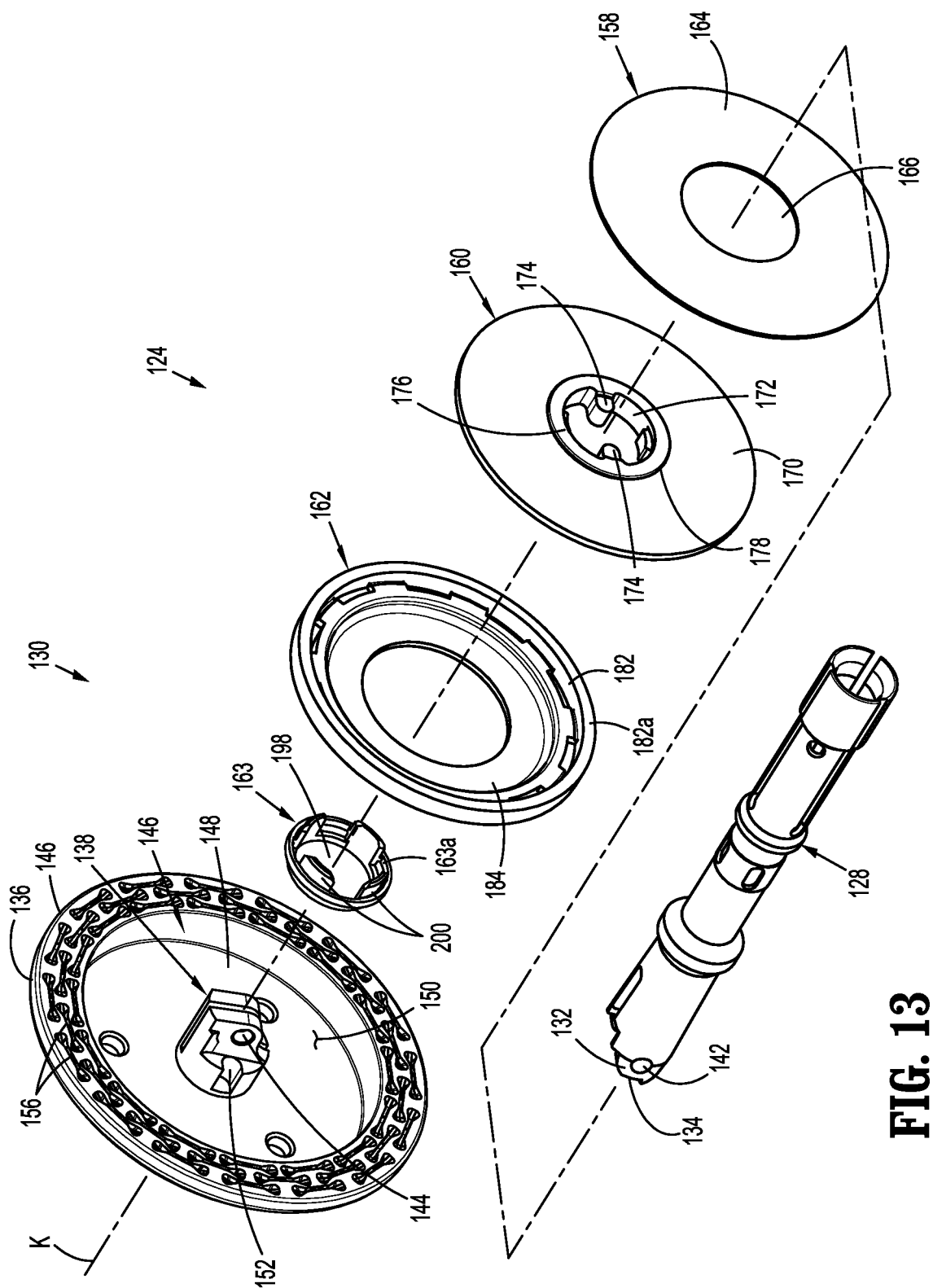
FIG. 13 is an exploded, perspective view of the anvil assembly shown in FIG. 12.

FIGS. 12 and 13 illustrate another exemplary embodiment of the anvil assembly shown generally as anvil assembly 124. The anvil assembly 124 also shares some common features with the anvil assembly disclosed in the '132 Patent and includes an anvil center rod 128 and an anvil head 130 pivotally mounted to the anvil center rod 128. The anvil center rod 128 includes a pair of spaced arms 132 with distal shelves 134. The anvil head 130 is adapted to pivot relative to the anvil center rod 128 between a first operative condition in opposition to the cartridge assembly 22 (FIG. 1) and a second pivoted or tilted condition (FIG. 11), and may be normally biased to the second titled condition via a spring-biased plunger mechanism (not shown). The anvil head 130 includes an anvil housing 136 having an internal anvil post 138 which is at least partially received within the spaced arms 132 (FIG. 13) of the anvil center rod 128. A pivot pin 140 (FIG. 18) extends through respective transverse bores 142, 144 (FIG. 13) of the spaced arms 132 and the anvil post 138 to pivotally couple the anvil head 130 to the anvil center rod 128.

The anvil housing 136 defines a central longitudinal axis "k" (FIG. 13) along which the anvil post 138 extends. The anvil housing 136 includes an internal housing wall 146 defining a distal wall surface 148 which supports the anvil post 138 and defines an internal housing recess 150. In embodiments, the anvil post 138 includes at least one keyed slot 152 and, in some embodiments, diametrically opposed keyed slots 152. The anvil housing 136 includes an outer tissue contact surface 154 circumscribing the internal housing recess 150. The outer tissue contact surface 154 supports tissue end margins of a tubular organ section, and defines a plurality of staple deforming pockets 156 that are positioned to receive and deform staples ejected from the cartridge housing 26 of the cartridge assembly 22.

The anvil head 130 includes, from proximal to distal, a cut ring 158, a backup member 160, an outer frangible or deformable retainer 162, and an inner frangible or deformable retainer 163. Each of the retainers 162, 163 is disposed within the internal housing recess 150 of the anvil housing 136 and is coaxially arranged about the anvil post 138 (FIG. 3). The cut ring 158 includes a disc-shaped annular body 164 that defines a central aperture 166 for reception of the anvil post 138. The cut ring 158 is at least partially penetrated by the annular knife 68 during firing of the stapling instrument 10 (FIG. 1) such that the tissue end margins overlying the cut ring 158 are severed by the annular knife 68 to create a passage through the anastomosed tubular organ sections. In embodiments, the cut ring 158 is formed through a molding process, e.g., an injection molding process, and may be fabricated from a material having a durometer which permits the annular knife 68 to pierce completely through the annular body 164 and bottom out against the backup member 160. Suitable materials for forming the cut ring 158 include polypropylene and polyester. Other materials are also contemplated.

The backup member 160 is configured for longitudinal movement relative to the anvil housing 136 from an initial longitudinal position to an advanced longitudinal position upon movement of the annular knife 68 (FIG. 4) within the internal housing recess 150 of the anvil housing 136 toward its actuated position. The backup member 160 includes an outer plate segment 170 that defines a central aperture 172 dimensioned for positioning about the anvil post 138 of the anvil housing 136. The backup member 160 includes a pair of diametrically opposed fingers 174 that extend radially inwardly from the outer plate segment 170 into the central aperture 172. The fingers 174 are at least partially received within the diametrically opposed keyed slots 152 of the anvil post 138 to align and/or guide the backup member 160 relative to the anvil housing 136 during movement of the backup member 160 between its initial longitudinal position and its advanced longitudinal position. The fingers 174 also engage the distal shelves 134 (FIG. 13) of the spaced arms 132 of the anvil center rod 128 to prevent pivotal movement of the anvil head 130 about the pivot pin 140 and retain the anvil head 130 in a first operative condition in opposition to the cartridge assembly 22 prior to firing of the stapling instrument 10 (FIG. 1).

The proximal side of the outer plate segment 170 of the backup member 160 includes a proximal raised flange 176 circumscribing the central aperture 172 which is received within the central aperture 166 of the cut ring 158. The proximal raised flange 176 of the backup member 160 may be press fit within the central aperture 166 of the cut ring 158 to secure these components to each other. In embodiments, the proximal raised flange 176 includes a lip 178 (FIG. 18) that overhangs an inner circumference of the cut ring 158 when the cut ring is coupled to the backup member 160. Alternatively, or in addition to, the backup member 160 and the cut ring 158 may be coupled together with cements, adhesives, using a spot welding process or the like. In embodiments, the backup member 160 is formed from a rigid material such as a metal, e.g., stainless steel.

Figure 14:
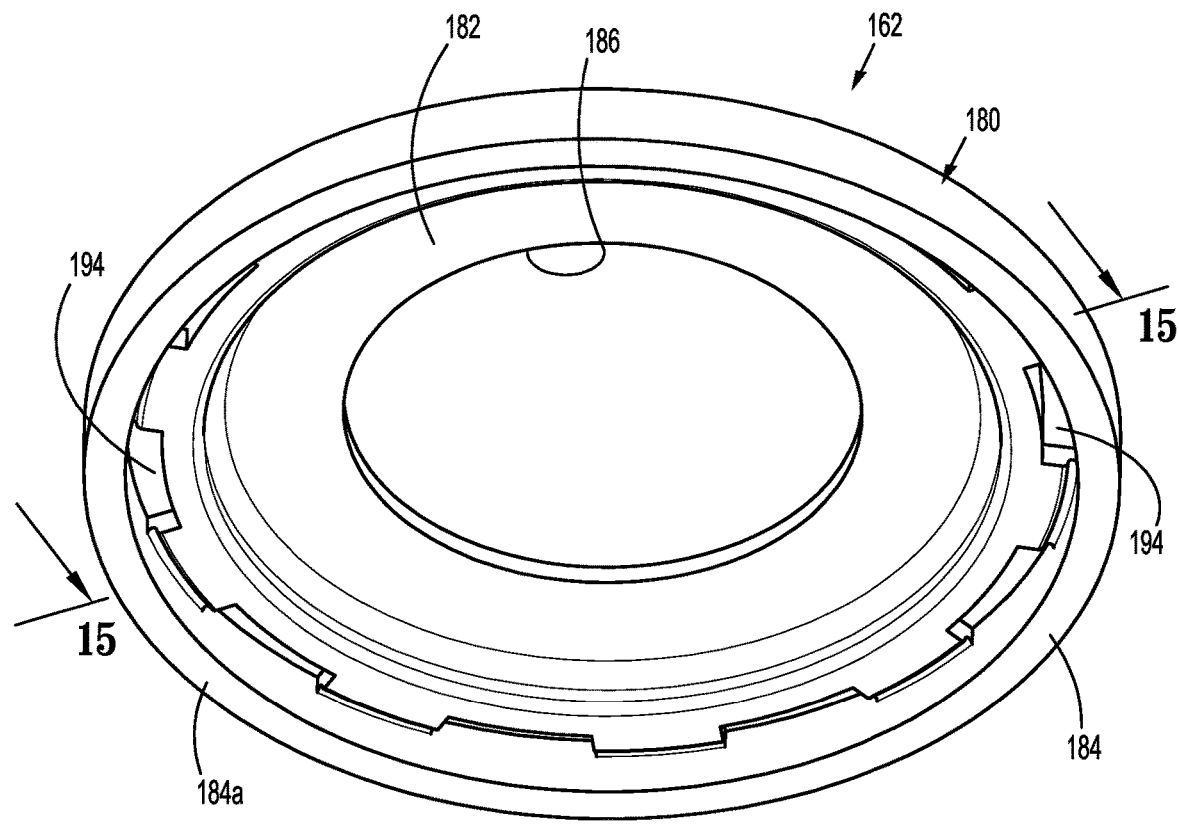
FIG. 14 is a side perspective view of an outer frangible ring of the anvil assembly shown in FIG. 13.
Figure 15:
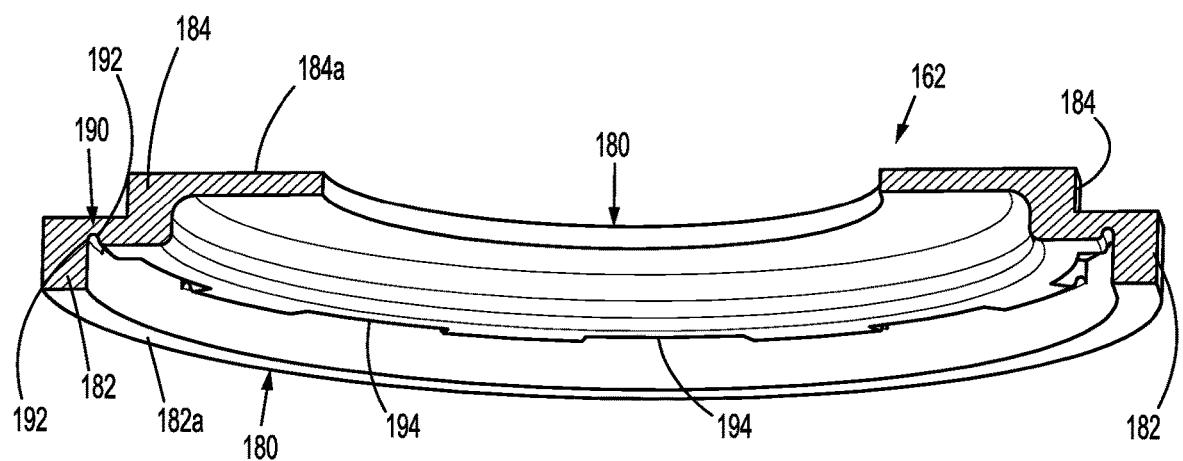
FIG. 15 is a cross-sectional view taken along section line 17-17 of FIG. 16.
Figure 19:
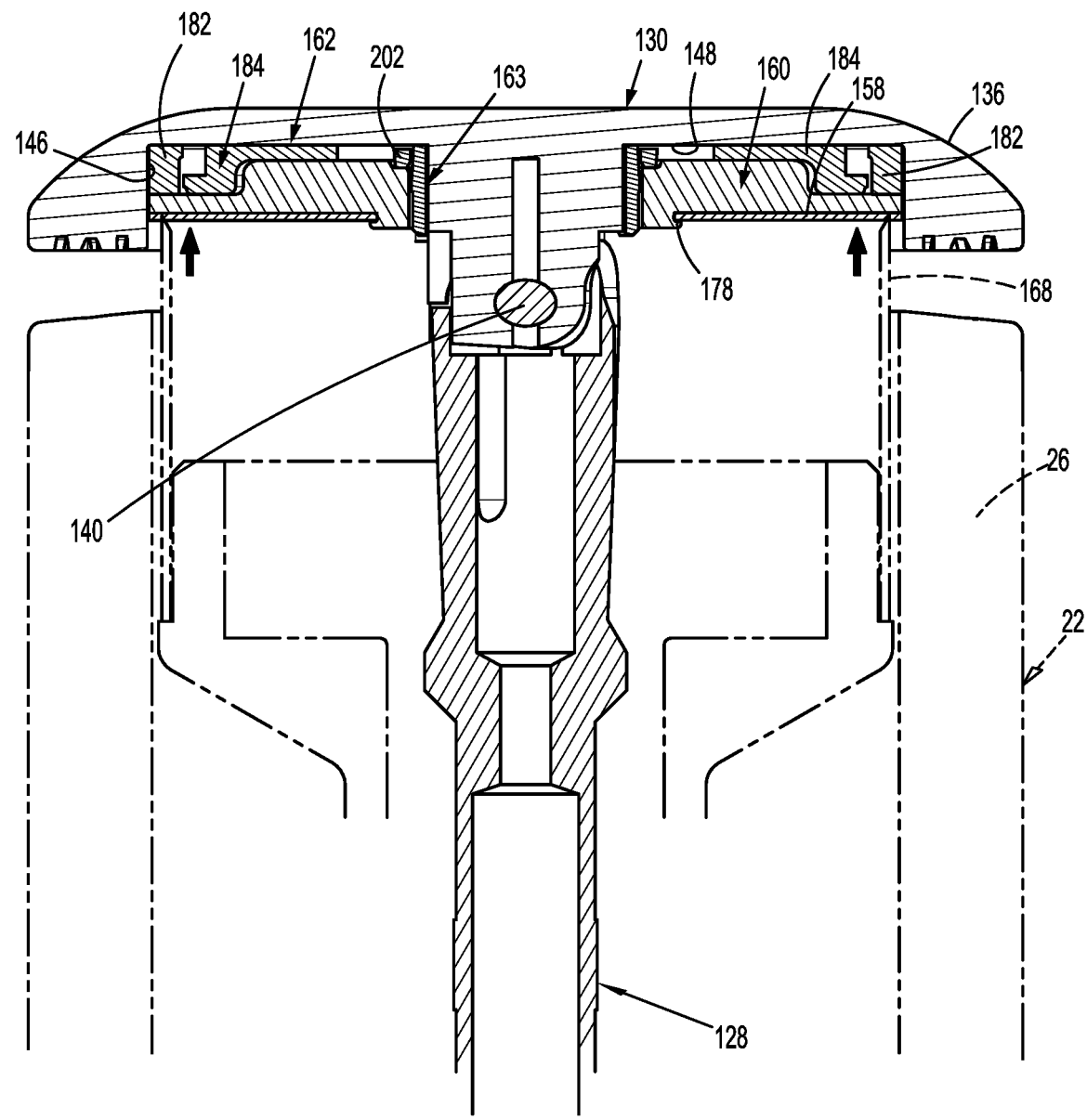
FIG. 19 is a cross-sectional view taken along section line 18-18 of FIG. 12 with the back-up ring in an advanced position within the anvil head.
Figure 20:
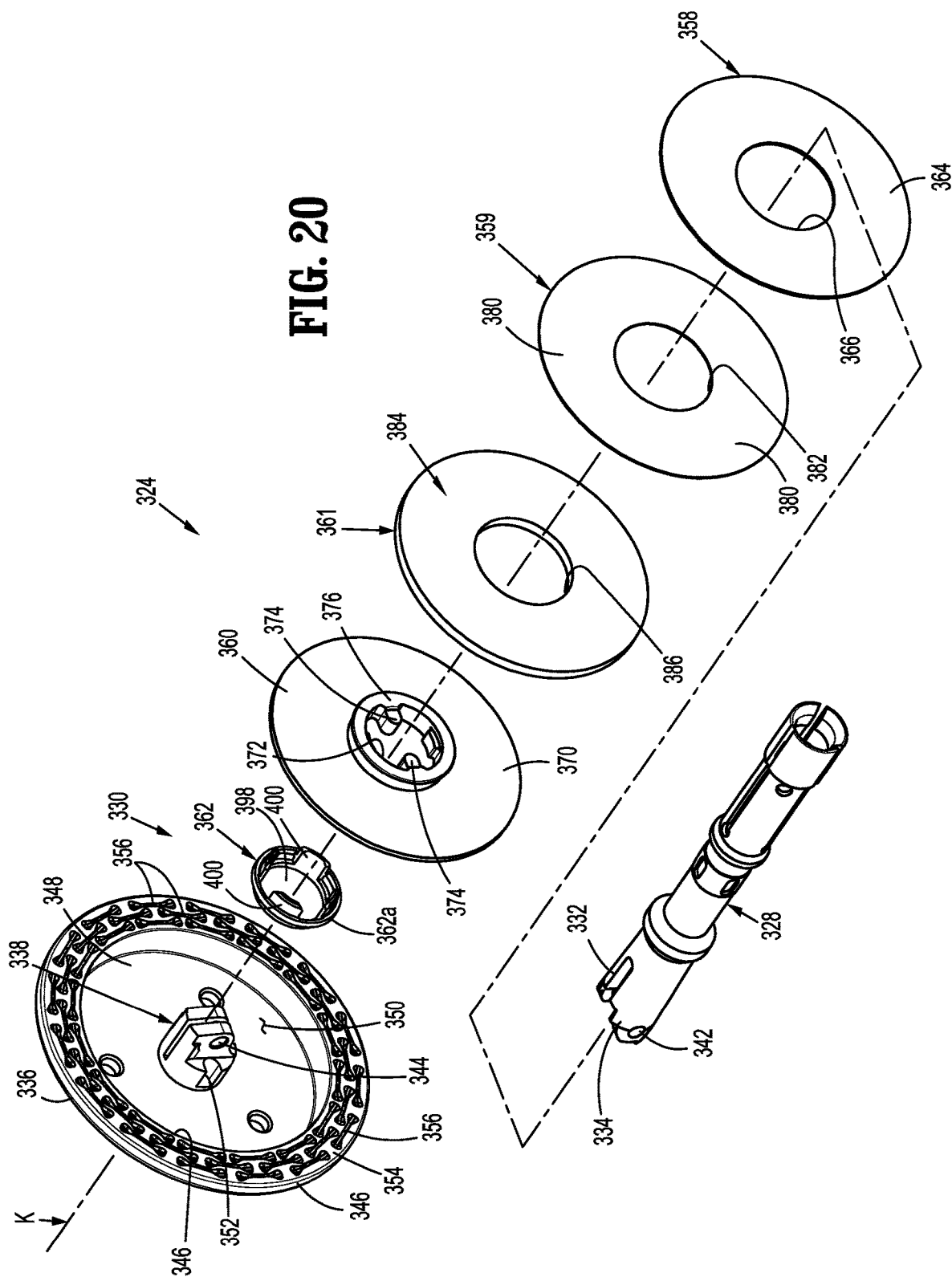
FIG. 20 is an exploded, perspective view of another exemplary embodiment of the anvil assembly of the stapling instrument shown in FIG. 1.

FIGS. 13-15 illustrate the outer frangible or deformable retainer 162. The retainer 162 includes a stepped body 180 that includes a proximal step 182 and a distal step 184. The distal step 184 is positioned radially inward of the proximal step and defines a central aperture 186 that receives the anvil post 138. The distal step 184 defines an abutment surface 184a (FIG. 15) that abuts the distal wall surface 148 of the anvil housing 136 (FIG. 19). The proximal step 182 defines a support surface 182a (FIG. 15) and includes a frangible or deformable portion 190. The support surface 182a supports the outer circumference of the outer plate segment 170 of the backup plate 160 and the frangible or deformable portion 190 is positioned between the abutment surface 184a and the support surface 182a. The frangible or deformable portion 190 is configured to fracture or deform when a force is applied in the distal direction on the backup member 160 as described in further detail below. In embodiments, the frangible portion 190 may include an annular groove 192 (FIG. 15) and/or a series of cutouts 194.

Figure 18:
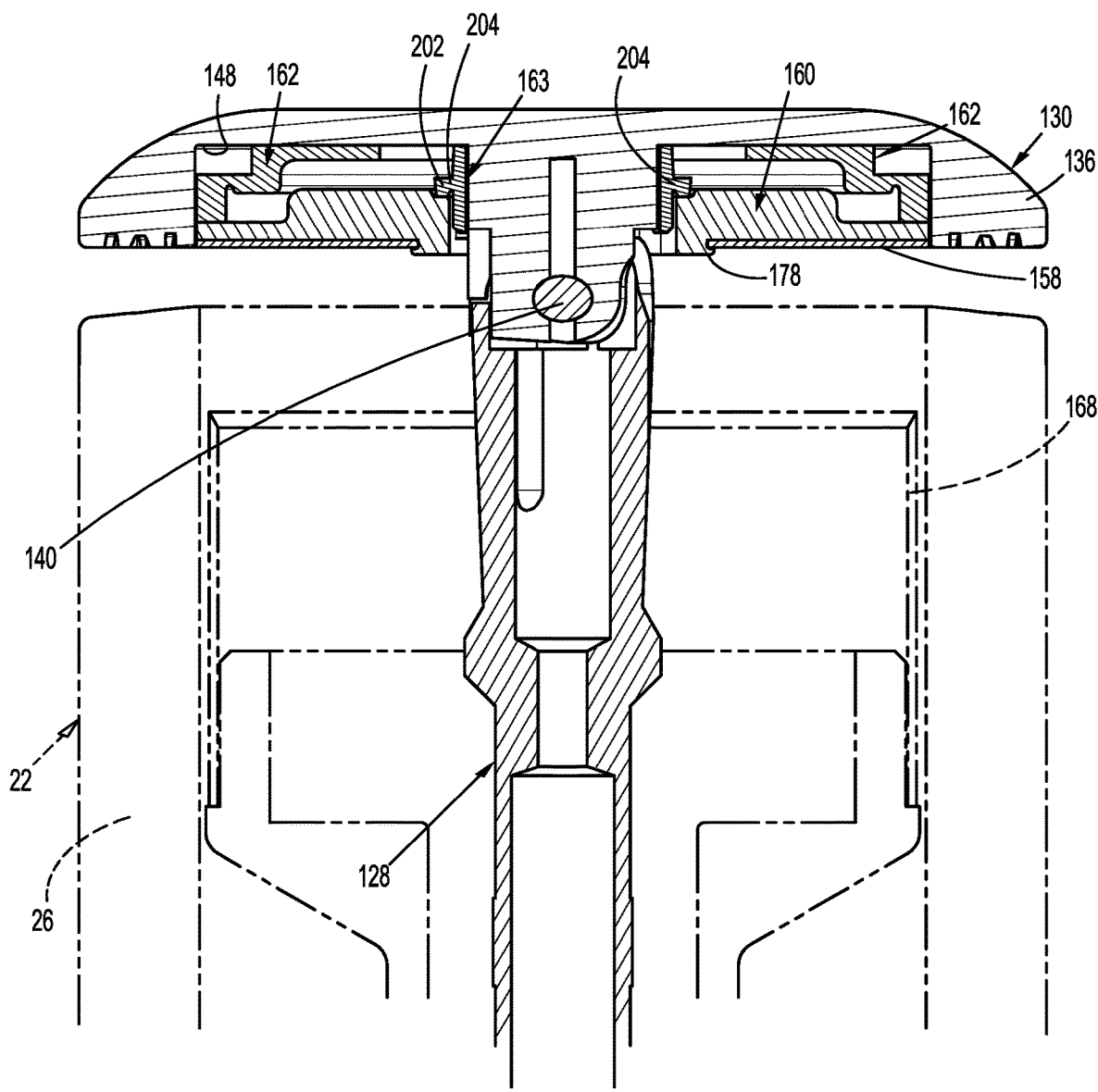
FIG. 18 is a cross-sectional view taken along section line 18-18 of FIG. 12 with the back-up ring in a retracted position within the anvil head.

The inner frangible or deformable retainer 163 is illustrated in FIG. 13 and includes an annular body 163a that defines a central aperture 198 and includes a plurality (e.g., four) of tabs 200 that extend in a proximal direction into and/or through the central aperture 172 of the backup member 160. The body 163a includes a distal portion that is abutting relation to the distal wall surface 148 of the anvil housing 136. The tabs 200 stabilize the retainer 163 relative to the backup member 160. A support member 202 is coupled to the annular body 163a and/or the tabs 200 and is arranged in coaxial relationship with respect to the central longitudinal axis "k". In some embodiments, the support member 202 includes a plurality of spaced support members 202. In embodiments, each of the plurality of support members 202 is coupled to a respective tab 200 via a connecting segment 204 (FIG. 18) that extends between a respective tab 200 and the support member 202. The connecting segments 204 define breakaway zones along which the inner support member 202 deforms or fragments relative to the tabs 200 upon actuation of the annular knife 68 (FIG. 18). The support member 202 supports the inner circumference of the backup member 160 and is spaced from the distal wall surface 148 of the anvil housing to retain the backup member 160 in its initial longitudinal position (FIG. 18) until a force is applied to the backup member 160 by the knife 68 (FIG. 18) to fracture or deform the inner support member 202.

The retainers 162 and 163 may be monolithically formed of a suitable elastomeric or metallic material.

Figure 16:
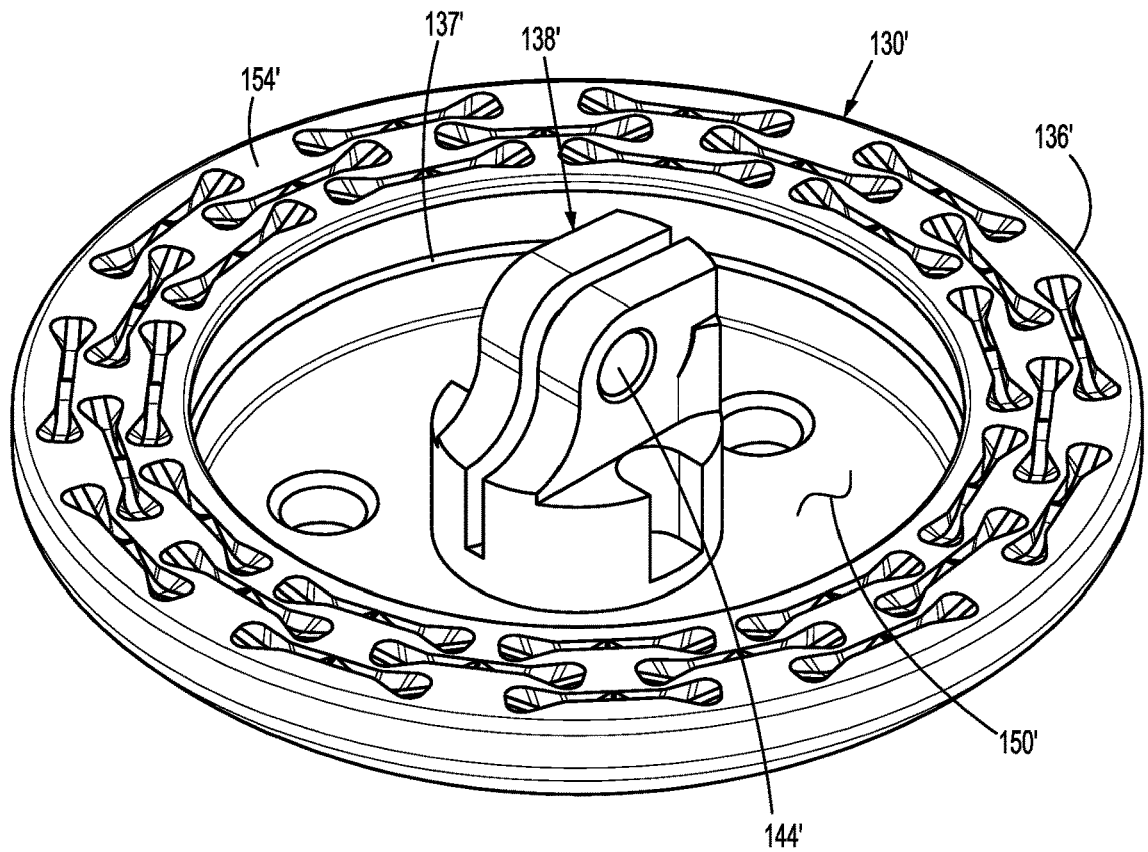
FIG. 16 is side perspective view of an anvil head of an anvil assembly in the Prior Art.
Figure 17:
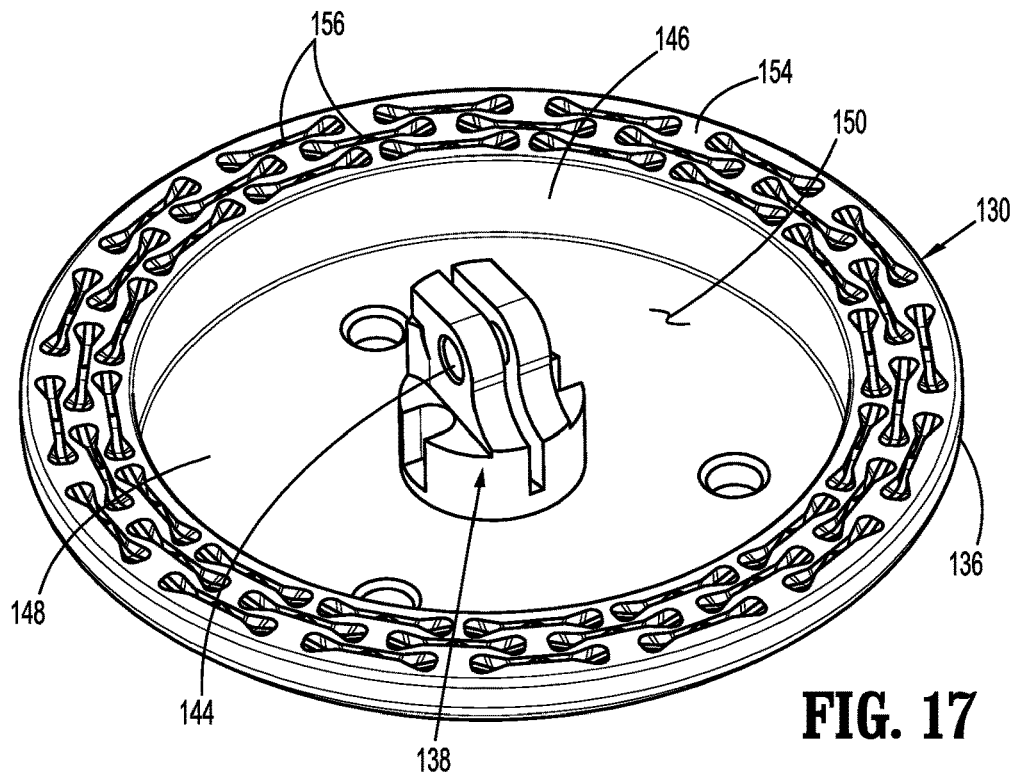
FIG. 17 is a side perspective view of the anvil head of the anvil assembly shown in FIG. 13.

Referring to FIGS. 16 and 17, "Prior Art" anvil housings 136' (FIG. 16) of the anvil head 130' typically include an undercut 137' (FIG. 16) along a wall defining the cavity 150'. The undercut 137' is provided to support an outer circumference of the backup plate 160'. With the disclosed anvil assembly 124, the need for an undercut 137' is obviated, as shown by the anvil housing 136 of FIG. 17, by providing the outer retainer 162 which includes the support surface 182a for supporting the outer circumference of the backup member 160 prior to firing of the stapling instrument 10 (FIG. 1). This substantially reduces manufacturing costs of forming the anvil housing 136.

FIGS. 18 and 19 illustrate the use of the end effector 16 (FIG. 1) including the anvil assembly 124. The tissue end margins of the tubular organ sections to be joined are placed about the anvil head 130 and the cartridge housing 26 of the cartridge assembly 22, respectively and secured via a purse string stitch or any other conventional methodology. The anvil head 130 and the cartridge assembly 22 are approximated. The stapling instrument 10 (FIG. 1) is then fired to eject the staples from the cartridge assembly 22 for passage through the tissue end margins of the tubular organ sections and deformation against the staple deforming pockets 156 of the anvil housing 136. The stapling instrument 10 (FIG. 1) is actuated to advance the annular knife 68 from the unactuated position of FIG. 18 in which the cutting edge of the annular knife 68 is positioned within the cartridge assembly 22 to the actuated position of FIG. 19 in which the cutting edge of the annular knife 68 is positioned extends through the tissue end margins and at least partially or completely through the cut ring 158. As the annular knife 68 advances, the annular knife 68 engages the cut ring 158 and advances cut ring 158 and the backup member 160 toward their advanced longitudinal positions. This motion exerts a force on the deformable portion 190 of the outer retainer 162 defined between the proximal step 182 and the distal step 184 of the outer retainer 162 and on the connecting segments 204 of the inner retainer 162 to fracture or deform these structures. When these structures fracture or deform, the backup member 160 and the cut ring 158 advance along the anvil post 138 with the fingers 174 of the backup member 160 traversing the keyed slots 152 of the anvil post 138. This movement releases the fingers 174 from engagement with the distal shelves 134 of the spaced arms 132 of the anvil center rod 128. When this occurs, the anvil head 130 is free to pivot from the first operative condition in which the anvil head 30 is in opposition to the cartridge assembly 22 (FIG. 19) to a second tilted condition (FIG. 10). As described above in regard to anvil assembly 24 (FIG. 2), a spring biased plunger mechanism may be associated with the anvil center rod 128 to bias the anvil head 130 to pivot about the pivot pin 40 to assume the second tilted condition.

FIGS. 20-23 illustrate another exemplary embodiment of the anvil assembly shown generally as anvil assembly 324. The anvil assembly 324 also shares some common features with the anvil assembly disclosed in the '132 Patent and includes an anvil center rod 328 and an anvil head 330 pivotally mounted to the anvil center rod 328. The anvil center rod 328 includes a pair of spaced arms 332 with distal shelves 334. The anvil head 330 is adapted to pivot relative to the anvil center rod 328 between a first operative condition in opposition to the cartridge assembly 22 (FIG. 1) and a second pivoted or tilted condition (FIG. 11), and may be normally biased to the second titled condition via a spring-biased plunger mechanism (not shown). The anvil head 330 includes an anvil housing 336 having an internal anvil post 338 which is at least partially received within the spaced arms 332 of the anvil center rod 328. A pivot pin 340 (FIG. 21) extends through respective transverse bores 342, 344 (FIG. 20) of the spaced arms 332 and the anvil post 338 to pivotally couple the anvil head 330 to the anvil center rod 328.

Figure 21:
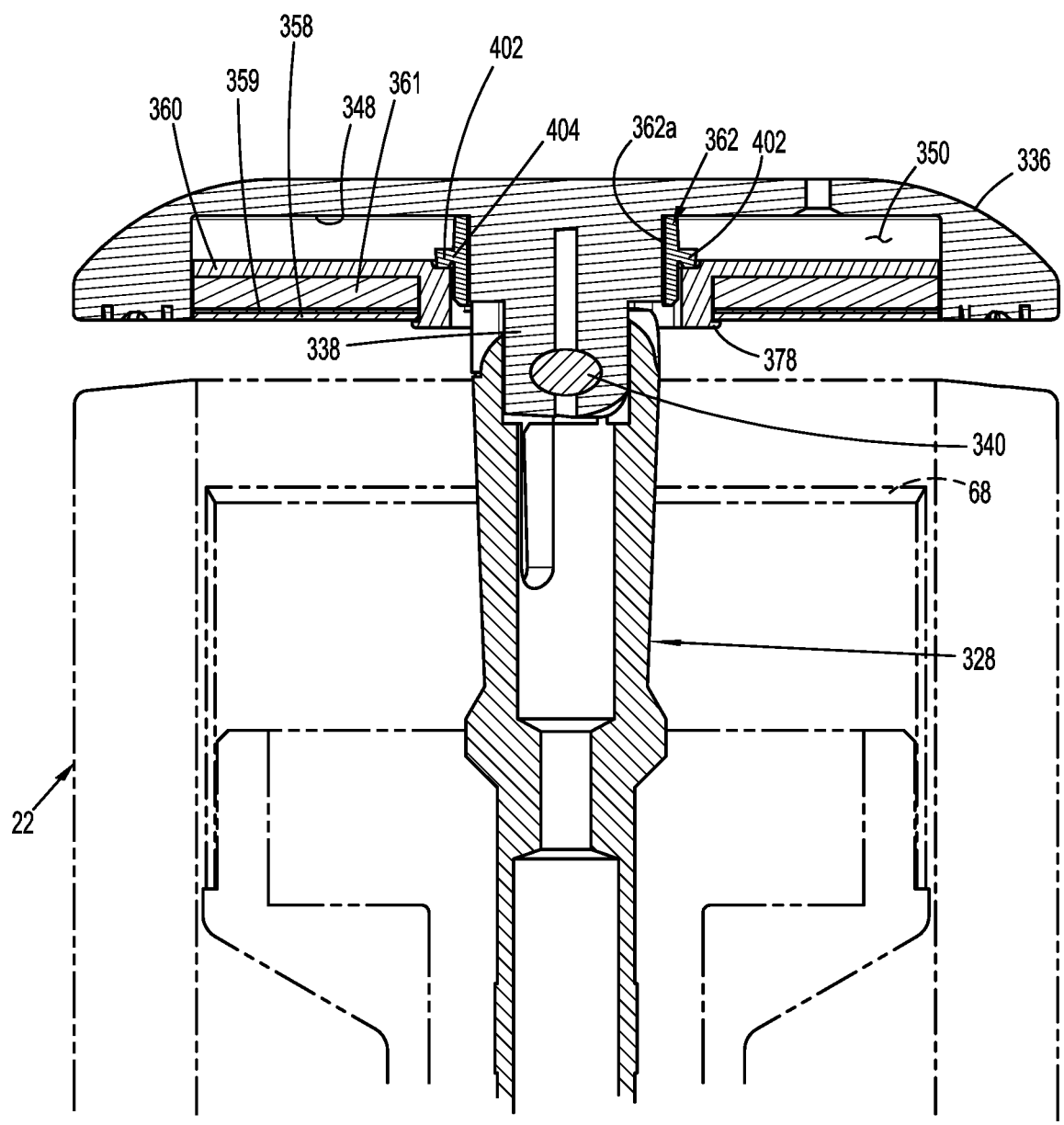
FIG. 21 is a side cross-sectional view taken through the anvil assembly shown in FIG. 20 with the back-up ring in a retracted position within the anvil head of the anvil assembly.

The anvil housing 336 defines a central longitudinal axis "k" (FIG. 20) along which the anvil post 338 extends. The anvil housing 336 includes an internal housing wall 346 defining a distal wall surface 348 which supports the anvil post 338 and defines an internal housing recess 350. In embodiments, the anvil post 338 includes at least one keyed slot 352 and, in some embodiments, diametrically opposed keyed slots 352. The anvil housing 336 includes an outer tissue contact surface 354 circumscribing the internal housing recess 350. The outer tissue contact surface 354 supports tissue end margins of a tubular organ section, and defines a plurality of staple deforming pockets 356 that are positioned to receive and deform staples ejected from the cartridge housing 26 of the cartridge assembly 22 (FIG. 21).

The anvil head 330 includes, from proximal to distal, a cut ring 358, a thin metal backup washer 359, a compliant washer 361, a backup member 360, and an inner frangible or deformable retainer 362. The retainer 362 is disposed within the internal housing recess 350 of the anvil housing 336 and is coaxially arranged about the anvil post 338 (FIG. 3). The cut ring 358 includes a disc-shaped annular body 364 that defines a central aperture 366 for reception of the anvil post 338. The cut ring 358 is at least partially penetrated by the annular knife 68 (FIG. 22) during firing of the stapling instrument 10 (FIG. 1) such that the tissue end margins overlying the cut ring 358 are severed by the annular knife 68 to create a passage through the anastomosed tubular organ sections. In embodiments, the cut ring 358 is formed through a molding process, e.g., an injection molding process, and may be fabricated from a material having a durometer which permits the annular knife 68 to pierce completely through the annular body 364 of the cut ring 358 and engage the backup washer 359 as described in further detail below. Suitable materials include polypropylene and polyester. Other materials are also contemplated.

The backup washer 359 is sandwiched between the cut ring 358 and the compliant washer 361 and includes a body 380 defining a central aperture 382 that receives the anvil post 338. The compliant washer 361 also includes a body 384 defining a central aperture 386 that receives the anvil post 338. The backup washer 359 is secured to a distal face of the compliant washer 361 using, for example, adhesive, cement or the like. In embodiments, the backup washer 359 is formed from a thin sheet of hard material such as stainless steel and the compliant washer 361 is formed from a compliant material such as rubber. When the annular knife 68 of the stapling instrument 10 engages the cut ring 358 when the stapling instrument 10 (FIG. 1) is fired, the annular knife 68 will penetrate the cut ring 358 and engage and deform the thin backup washer 359 into the compliant washer 361 as tissue is being cut. Deforming of the thin backup washer 359 into the compliant washer 361 will allow for an uneven knife 68 to cut tissue around the entire diameter of the anvil head 330.

The backup member 360 is configured for longitudinal movement relative to the anvil housing 336 from an initial longitudinal position to an advanced longitudinal position upon movement of the annular knife 68 (FIG. 21) within the internal housing recess 350 of the anvil housing 336 toward its actuated position. The backup member 360 includes an outer plate segment 370 that defines a central aperture 372 dimensioned for positioning about the anvil post 338 of the anvil housing 336. The backup member 360 includes a pair of diametrically opposed fingers 374 that extend radially inwardly from the outer plate segment 370 into the central aperture 372. The fingers 374 are at least partially received within the diametrically opposed keyed slots 352 (FIG. 20) of the anvil post 338 to align and/or guide the backup member 360 relative to the anvil housing 336 during movement of the backup member 360 between its initial longitudinal position and its advanced longitudinal position. The fingers 374 also engage the distal shelves 334 (FIG. 20) of the spaced arms 332 of the anvil center rod 328 to prevent pivotal movement of the anvil head 330 about the pivot pin 340 and retain the anvil head 330 in a first operative condition in opposition to the cartridge assembly 22 prior to firing of the stapling instrument 10 (FIG. 1).

The proximal side of the outer plate segment 370 of the backup member 360 includes a proximal raised flange 376 circumscribing the central aperture 372 which is received within the central aperture 366 of the cut ring 358, and the central apertures 386, 382, 366 of the compliant washer 361, the backup washer 359, and the cut ring 358, respectively. The proximal raised flange 376 of the backup member 360 may be press fit within the central aperture 386, 382, 366 to secure these components to each other. In embodiments, the proximal raised flange 376 includes a lip 378 (FIG. 18) that overhangs an inner circumference of the cut ring 358 when the cut ring 358 is coupled to the backup member 360. Alternatively, or in addition to, the backup member 360 and the compliant washer 361, the backup washer 361, and the cut ring 358 may be coupled together with cements, adhesives, a spot welding process or the like.

The inner frangible or deformable retainer 362 includes an annular body 362a that defines a central aperture 398 and includes a plurality (e.g., four) of tabs 400 that extend in a proximal direction into the central aperture 372 of the backup member 360. The body 362a includes a distal portion that is abutting relation to the internal wall surface 348 of the anvil housing 336. The tabs 400 stabilize the retainer 362 relative to the backup member 360. A support member 402 is coupled to the tabs 400 and arranged in coaxial relationship with respect to the central longitudinal axis "k". In embodiments, the support member 402 may include a plurality of spaced support members 402 which are coupled to the respective tabs 400 via a connecting segment 404 (FIG. 21) that extends between respective tabs 400 and the support member 402. The connecting segments 404 define breakaway zones along which the support members 402 deform or fragment relative to the tabs 400 upon actuation of the annular knife 68 (FIG. 18). The support members 402 support the inner circumference of the backup member 360 and are spaced from the distal wall surface 348 of the anvil housing 336 to retain the backup member 360 in its initial longitudinal position (FIG. 21) until a force is applied to the backup member 360 by the annular knife 68 (FIG. 22) to fracture or deform the support members 402.

Figure 22:
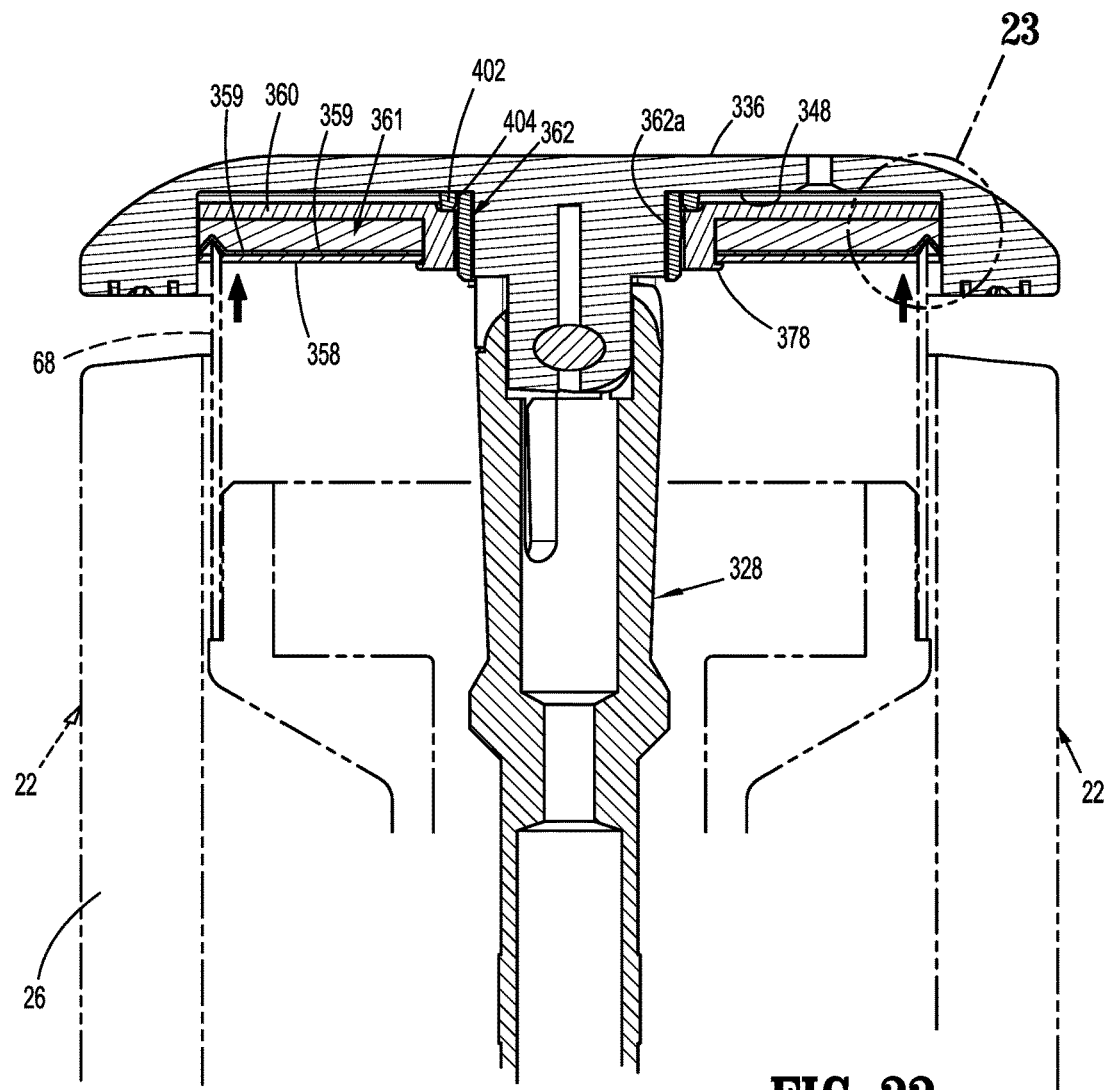
FIG. 22 is a side cross-sectional view taken through the anvil assembly shown in FIG. 20 with the back-up ring in an advanced position within the anvil head of the anvil assembly.
Figure 23:
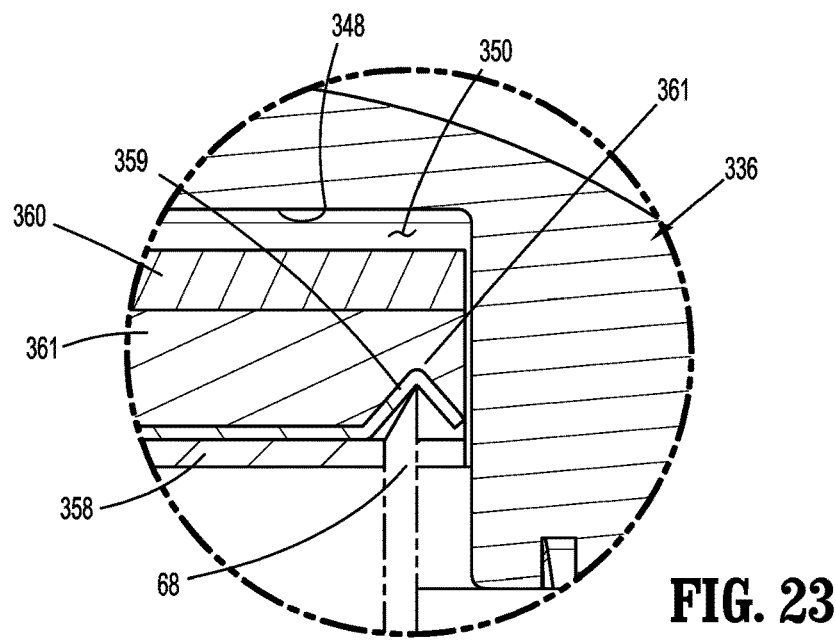
FIG. 23 is an enlarged view of the indicated area of detail shown in FIG. 22.

FIGS. 21-23 illustrate the use of the end effector 16 (FIG. 1) including the anvil assembly 324. As described above in regard to anvil assemblies 24 and 124, tissue end margins of the tubular organ sections to be joined are secured about the anvil head 130 and the cartridge housing 26 of the cartridge assembly 22 and the anvil head 330 and the cartridge assembly 22 are approximated. When stapling instrument 10 (FIG. 1) is fired the annular knife 68 is advanced from its unactuated position of FIG. 21 in which the cutting edge of the annular knife 68 is positioned within the cartridge assembly 22 to the actuated position of FIG. 22 in which the annular knife 68 extends through the tissue end margins and through the cut ring 358. As the annular knife 68 advances, the backup member 360 is advanced toward its advanced longitudinal position. This motion exerts a force on the connecting segments 404 of the inner retainer 162 to fracture or deform the connecting segments 404. When the connecting segments 404 fracture or deform, the backup member 360, the compliant washer 361, the backup washer 359, and the cut ring 358 advance along the anvil post 338 with the fingers 374 of the backup member 360 traversing the keyed slots 352 of the anvil post 338. This movement releases the fingers 374 from their engagement with the distal shelves 334 of the spaced arms 332 of the anvil center rod 328. When this occurs, the anvil head 130 is free to pivot from the first operative condition in which the anvil head 30 is in opposition to the cartridge assembly 22 (FIG. 19) to a second tilted condition (FIG. 10). As described above in regard to anvil assembly 24 (FIG. 2), a spring biased plunger mechanism may be associated with the anvil center rod 128 to bias the anvil head 130 to pivot about the pivot pin 40 to assume the second tilted condition.

When the backup member 360 reaches its advanced longitudinal position within the anvil housing 336, the annular knife 68 will continue to advance distally through the cut ring 358 and into the backup washer 359. As the annular knife 68 advances, the backup washer 359 will deform inwardly into the compliant washer 361. As described above, this deformation allows for a knife 68 having an uneven cutting edge to cut tissue around the entire diameter of the anvil head 330 and also allows the knife 68 to cut through staples that may be positioned in the path of the knife 68.

Persons skilled in the art will understand that the instruments and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical anvil assembly for use with a circular stapling instrument, comprising:
   an anvil center rod;
   an anvil head pivotally coupled to the anvil center rod and movable between a first operative condition and a second tilted condition, the anvil head including:
      an anvil housing defining a central longitudinal axis;
      a backup member disposed within the anvil housing, the backup member configured for longitudinal movement relative to the anvil housing from an initial longitudinal position retaining the anvil head in the first operative condition to an advanced longitudinal position permitting pivotal movement of the anvil head to the second tilted condition, the backup member including an outer plate segment having a plurality of force transfer projections; and
      a retainer positioned in the anvil housing adjacent the backup member, the retainer configured to retain the backup member in the initial longitudinal position, the retainer including an outer retainer segment defining an outer deformable region in general longitudinal alignment with the force transfer projections of the backup member, the outer deformable region configured to be engaged by the force transfer projections of the backup member and at least partially deform upon application of a predetermined longitudinal force to the backup member to permit the backup member to move to the advanced longitudinal position.

2. The anvil assembly according to claim 1 wherein the anvil housing includes a housing wall, the retainer being at least partially positioned between the housing wall and the backup member.

3. The anvil assembly according to claim 2 wherein the force transfer projections of the backup member are coaxially arranged with respect to the central longitudinal axis.

4. The anvil assembly according to claim 3 wherein the outer deformable region of the retainer is coaxially arranged about the central longitudinal axis.

5. The anvil assembly according to claim 4 wherein the outer retainer segment includes at least two grooves defined therein, the outer deformable region being defined at least in part between the two grooves.

6. The anvil assembly according to claim 5 wherein the at least two grooves are annular and coaxially arranged about the central longitudinal axis.

7. The anvil assembly according to claim 2 wherein the outer deformable region is configured to fracture relative to the outer retainer segment upon engagement with the force transfer projections of the backup member upon application of the predetermined longitudinal force to the backup member.

8. The anvil assembly according to claim 2 wherein the retainer includes an inner deformable ring radial inward of the outer deformable region, the inner deformable ring configured to be engaged by the backup member and at least partially deform upon application of the predetermined longitudinal force to the backup member.

9. The anvil assembly according to claim 8 wherein the inner deformable ring is configured to fracture upon application of the predetermined longitudinal force to the backup member.

10. The anvil assembly according to claim 2 including a cut ring positioned adjacent the backup member.

11. The anvil assembly according to claim 10 wherein the anvil head includes an anvil post depending from the housing wall, wherein the retainer, the backup member and the cut ring are coaxially mounted about the anvil post.

12. An end effector for use with a circular stapling instrument, comprising:
  a cartridge assembly including a cartridge housing and an annular knife, the annular knife configured for advancing movement from an unactuated position to an actuated position; and
  an anvil assembly mountable relative to the cartridge assembly, the anvil assembly including:
    an anvil center rod; and
    an anvil head pivotally coupled to the anvil center rod and movable between a first operative condition and a second tilted condition, the anvil head including:
      an anvil housing defining a central longitudinal axis;
      a backup member disposed within the anvil housing, the backup member configured for longitudinal movement relative to the anvil housing from an initial longitudinal position retaining the anvil head in the first operative condition to an advanced longitudinal position permitting pivotal movement of the anvil head to the second tilted condition upon advancing movement of the annular knife toward the actuated position, the backup member including an outer plate segment having a plurality of force transfer projections coaxially arranged with respect to the central longitudinal axis; and
      a retainer positioned in the anvil housing adjacent the backup member, the retainer configured to retain the backup member in the initial longitudinal position, the retainer including an outer retainer segment defining an annular deformable region coaxially arranged with respect to the central longitudinal axis and in general longitudinal alignment with the force transfer projections of the backup member, the annular deformable region configured to be engaged by the force transfer projections of the backup member and at least partially deform upon advancing movement of the annular knife toward the actuated position to permit the backup member to move to the advanced longitudinal position.

13. The end effector according to claim 12 wherein the retainer includes an inner deformable ring radial inward of the annular deformable region, the inner deformable ring configured to be engaged by the backup member and at least partially deform upon advancing movement of the annular knife toward the actuated position.

14. The end effector according to claim 13 wherein the annular deformable region and the inner deformable ring are each configured to fracture upon advancing movement of the annular knife toward the actuated position.

15. The end effector according to claim 12 wherein the backup member includes a pair of diametrically opposed fingers configured for engagement with the anvil center rod in the initial longitudinal position of the backup member and to maintain the anvil head in the first operative condition, and configured to release the anvil center rod upon movement to the advanced longitudinal position to permit pivoting movement of the anvil head to the second tilted condition.

16. A surgical anvil assembly for use with a circular stapling instrument, comprising:
  an anvil center rod;
  an anvil head pivotally coupled to the anvil center rod and movable between a first operative condition and a second tilted condition, the anvil head including:
    an anvil housing defining a central longitudinal axis and a cavity, the cavity defined by a distal wall surface;
    a backup member disposed within the anvil housing having an inner circumferential surface and an outer circumferential surface, the backup member movable from an initial longitudinal position in which the backup member retains the anvil head in the first operative condition to an advanced longitudinal position in which the backup member permits pivotal movement of the anvil head to the second tilted condition;
    an inner retainer positioned in the anvil housing adjacent the backup member, the inner retainer positioned to engage the inner circumferential surface of the backup member to retain the backup member in the initial longitudinal position, the inner retainer including a breakaway zone that is frangible upon application of a predetermined distal force on the backup member to permit movement of the backup member to the advanced longitudinal position; and
    an outer retainer positioned in the anvil housing adjacent the backup member, the outer retainer positioned to engage the outer circumferential surface of the backup member to retain the backup member in the initial longitudinal position, the outer retainer including a frangible portion that is frangible upon application of a predetermined distal force on the backup member to permit movement of the backup member to the advanced longitudinal position.

17. The surgical anvil assembly according to claim 16, wherein the inner retainer includes an annular body having a distal portion, the distal portion of the annular body positioned in abutting relation to the distal wall surface of the housing.

18. The surgical anvil assembly according to claim 17, wherein the inner retainer includes a support surface that supports the inner circumferential surface of the backup member, the support member coupled to the annular body by a connecting segment having the breakaway zone.

19. The surgical anvil assembly according to claim 18, wherein the support member includes a plurality of support members spaced about the annular body.

20. The surgical anvil assembly according to claim 16, wherein the outer retainer includes a body having a proximal step and a distal step, the distal step including an abutment surface positioned to abut the distal wall surface defining the cavity, and the proximal step including a support surface positioned to support the outer circumferential surface of the backup member.

21. The surgical anvil assembly according to claim 20, wherein the outer step includes the frangible portion.

22. The surgical anvil assembly according to claim 16, further including a cut ring supported on a distal face of the backup member.

23. A surgical anvil assembly for use with a circular stapling instrument, comprising:
   an anvil center rod;
   an anvil head pivotally coupled to the anvil center rod and movable between a first operative condition and a second tilted condition, the anvil head including:
   an anvil housing defining a central longitudinal axis and a cavity, the cavity defined by a distal wall surface;
   a backup member disposed within the anvil housing having an inner circumferential surface and an outer circumferential surface, the backup member movable from an initial longitudinal position in which the backup member retains the anvil head in the first operative condition to an advanced longitudinal position in which the backup member permits pivotal movement of the anvil head to the second tilted condition;
   a compliant washer supported on a distal face of the backup member;
   a backup washer supported on a distal face of the compliant washer, the backup washer formed of metal;
   a cut ring supported on a distal face of the backup washer;
   a retainer positioned in the anvil housing adjacent the backup member, the retainer positioned to engage the backup member to retain the backup member in the initial longitudinal position, the retainer being deformable or frangible upon application of a predetermined distal force on the backup member to permit movement of the backup member to the advanced longitudinal position;
   wherein the backup washer is configured to deform into the compliant washer upon application of a predetermined force on the backup washer.

24. The surgical anvil assembly according to claim 23, wherein the compliant washer is formed from rubber.

25. The surgical anvil assembly according to claim 24, wherein the backup washer is formed from stainless steel.

26. The surgical anvil assembly according to claim 23, wherein the retainer is positioned to engage the inner circumferential surface of the backup member.

* * * * *